(12) United States Patent
Pickkers et al.

(10) Patent No.: US 8,586,032 B2
(45) Date of Patent: Nov. 19, 2013

(54) USE OF ALKALINE PHOSPHATASE IN THE TREATMENT OF REDUCED RENAL FUNCTION

(75) Inventors: Roelof P. Pickkers, Nijmegen (NL);
Suzanne Heemskerk, Nijmegen (NL);
Markwin P. Velders, Bilthoven (NL);
Willem Raaben, Amersfoort (NL);
Marty B. F. Wulferink, Ede (NL)

(73) Assignee: AM-Pharma B.V., Bunnik (NL)

( * ) Notice: Subject to any disclaimer, the term of this patent is extended or adjusted under 35 U.S.C. 154(b) by 742 days.

(21) Appl. No.: 12/449,192

(22) PCT Filed: Jan. 30, 2008

(86) PCT No.: PCT/NL2008/050053
§ 371 (c)(1),
(2), (4) Date: Jan. 6, 2010

(87) PCT Pub. No.: WO2008/094037
PCT Pub. Date: Aug. 7, 2008

(65) Prior Publication Data
US 2010/0111923 A1    May 6, 2010

(30) Foreign Application Priority Data

Jan. 30, 2007 (EP) .................................... 07101437

(51) Int. Cl.
| | | |
|---|---|---|
| *A61K 38/46* | (2006.01) | |
| *C12N 9/00* | (2006.01) | |
| *C12N 9/16* | (2006.01) | |
| *C12N 1/20* | (2006.01) | |
| *C12N 15/00* | (2006.01) | |
| *C07H 21/04* | (2006.01) | |

(52) U.S. Cl.
USPC ....... 424/94.6; 435/183; 435/196; 435/252.3; 435/320.1; 536/23.2

(58) Field of Classification Search
None
See application file for complete search history.

(56) References Cited

U.S. PATENT DOCUMENTS

| 5,723,441 A | 3/1998 | Higley et al. |
| 2004/0115185 A1 | 6/2004 | Kiss |

FOREIGN PATENT DOCUMENTS

| CN | 1425766 A | | 6/2003 |
| EP | 1 132 086 A2 | | 9/2001 |
| WO | WO 2005/074978 | * | 8/2005 |
| WO | WO 2005-074978 A | | 8/2005 |
| WO | WO 2008/094037 A1 | | 8/2008 |

OTHER PUBLICATIONS

Peters et al. Pharmacol Exp Ther. Nov. 6, 2012 (Abstract).*
Leibovitch et al., Increased serum alkaline phosphatase activity: a possible indicator of renal damage, Journal of clinical Laboratory Analysis, 1991, pp. 406-409, vol. 5, No. 6.
PCT International Search Report, PCT/NL2008/050053, dated Mar. 18, 2008.
U.S. Appl. No. 10/395,031, filed Mar. 21, 2003, Inventor: van Ommen et al., Title: Induction of Exon Skipping in Eukaryotic Cells.
U.S. Appl. No. 11/233,495, filed Sep. 21, 2005, Inventor: van Ommen et al., Title: Modulation of Exon Recognition in Pre-MRNA by Interfering With the Secondary RNA Structure.
U.S. Appl. No. 11/233,507, filed Sep. 21, 2005, Inventor: van Ommen et al., Title: Modulation of Exon Recognition in Pre-MRNA by Interfering With the Secondary RNA Structure.
U.S. Appl. No. 11/982,285, filed Oct. 31, 2007, Inventor: van Ommen et al., Title: Induction of Exon Skipping in Eukaryotic Cells.
U.S. Appl. No. 12/231,028, filed Aug. 27, 2008, Inventor: Brouwer et al., Title: Mutants of Lactoferrin.
U.S. Appl. No. 12/383,897, filed Mar. 30, 2009, Inventor: van Oilmen et al., Title: Induction of Exon Skipping in Eukaryotic Cells.
Beumer, C. et al., Calf intestinal alkaline phosphatase, a novel therapeutic drug for lipopolysaccharide (LPS)—mediated diseases, attenuates LPS toxicity in mice and piglets, *Journal of Pharmacology and Experimental Therapeutics*, Nov. 2003, vol. 307 No. 2, pp. 737-744.
English language Abstract for CN1425766, Published Jun. 25, 2003 (cited herein as FPI),

* cited by examiner

*Primary Examiner* — Christian Fronda
(74) *Attorney, Agent, or Firm* — Sterne, Kessler, Goldstein & Fox P.L.L.C.

(57) ABSTRACT

The invention relates to the field of medicine and in particular to the use of alkaline phosphatase in the treatment of renal diseases, such as reduced renal function. The present invention also relates to the field of pharmacy and in particular to the pharmaceutical use of alkaline phosphatase. The present invention provides an alternative treatment to improve a situation in which the renal function is reduced by using alkaline phosphatase.

11 Claims, 12 Drawing Sheets

Fig. 10

NP_001623 ALPP (Placental)

```
  1 IIPVEEENPDFWNREAAEALGAAKKLQPAQTAAKNLIIFLGDGMGVSTVTAARILKGQKK  60
 61 DKLGPEIPLAMDRFPYVALSKTYNVDKHVPDSGATATAYLCGVKGNFQTIGLSAAARFNQ 120
121 CNTTRGNEVISVMNRAKKAGKSVGVVTTTRVQHASPAGTYAHTVNRNWYSDADVPASARQ 180
181 EGCQDIATQLISNMDIDVILGGGRKYMFRMGTPDPEYPDDYSQGGTRLDGKNLVQEWLAK 240
241 RQGARYVWNRTELMQASLDPSVTHLMGLFEPGDMKYEIHRDSTLDPSLMEMTEAALRLLS 300
301 RNPRGFFLFVEGGRIDHGHHESRAYRALTETIMFDDAIERAGQLTSEEDTLSLVTADHSH 360
361 VFSFGGYPLRGSSIFGLAPGKARDRKAYTVLLYGNGPGYVLKDGARPDVTESESGSPEYR 420
421 QQSAVPLDEETHAGEDVAVFARGPQAHLVHGVQEQTFIAHVMAFAACLEPYTACDLAPPA 480
481 GTTDAAHPGRSVVPALLPLLAGTLLLLETATAP 513
```

AAI32679 ALPI (Intestinal)

```
  1 VIPAEEENPAFWNRQAAEALDAAKKLQPIQKVAKNLILFLGDGLGVPTVTATRILKGQKN  60
 61 GKLGPETPLAMDRFPYLALSKTYNVDRQVPDSAATATAYLCGVKANFQTIGLSAAARFNQ 120
121 CNTTRGNEVISVMNRAKQAGKSVGVVTTTRVQHASPAGTYAHTVNRNWYSDADMPASARQ 180
181 EGCQDIATQLISNMDIDVILGGGRKYMFPMGTPDPEYPADASQNGIRLDGKNLVQEWLAK 240
241 HQGAWYVWNRTELMQASLDQSVTHLMGLFEPGDTKYEIHRDPTLDPSLMEMTEAALRLLS 300
301 RNPRGFYLFVEGGRIDHGHHEGVAYQALTEAVMFDDAIERAGQLTSEEDTLTLVTADHSH 360
361 VFSFGGYTLRGSSIFGLAPSKAQDSKAYTSILYGNGPGYVFNSGVRPDVNESESGSPDYQ 420
421 QQAAVPLSSETHGGEDVAVFARGPQAHLVHGVQEQSFVAHVMAFAACLEPYTACDLAPPA 480
481 CTTDAAHPVAASLPLLAGTLLLLGASAAP 509
```

P10696 GCAP (Germ-cell or Placental-like)

```
  1 IIPVEEENPDFWNRQAAEALGAAKKLQPAQTAAKNLIIFLGDGMGVSTVTAARILKGQKK  60
 61 DKLGPETFLAMDRFPYVALSKTYSVDKHVPDSGATATAYLCGVKGNFQTIGLSAAARFNQ 120
121 CNTTRGNEVISVMNRAKKAGKSVGVVTTTRVQHASPAGAYAHTVNRNWYSDADVPASARQ 180
181 EGCQDIATQLISNMDIDVILGGGRKYMFPMGTPDPEYPDDYSQGGTRLDGKNLVQEWLAK 240
241 HQGARYVWNRTELLQASLDPSVTHLMGLFEPGDMKYEIHRDSTLDPSLMEMTEAALLLLS 300
301 RNPRGFFLFVEGGRIDHGHHESRAYRALTETIMFDDAIERAGQLTSEEDTLSLVTADHSH 360
361 VFSFGGYPLRGSSIFGLAPGKARDRKAYTVLLYGNGPGYVLKDGARPDVTESESGSPEYR 420
421 QQSAVPLDGETHAGEDVAVFARGPQAHLVHGVQEQTFIAHVMAFAACLEPYTACDLAPRA 480
481 GTTDAAHPGPSVVPALLPLLAGTLLLLGTATAP 513
```

AAI10910 (Tissue Non Specific)

```
  1 LVPEKEKDPKYWRDQAQETLKYALELQKLNTNVAKNVIMFLGDGMGVSTVTAARILKGQL  60
 61 HHNPGEETRLEMDKFPFVALSKTYNTNAQVPDSAGTATAYLCGVKANEGTVGVSAATERS 120
121 RCNTTQGNEVTSILRWAKDAGKSVGIVTTTRVNHATPSAAYAHSADRDWYSDNEMPPEAL 180
181 SQGCKDIAYQLMHNIRDIDVIMGGGRKYMYPKNKTDVEYESDEKARGTRLDGLDVDTWK 240
241 SFKPRHKHSHFIWNRTELLTLDPHNVDYLLGLFEPGDMQYELNRNNVTDPSLSEMVVVAI 300
301 QILRKNPKGFFLLVEGGRIDHGHHEGKAKQALHEAVEMDRAIGQAGSLTSSEDTLTVVTA 360
361 DHSHVFTFGGYTPRGNSIFGLAPMLSDTDKKPFTAILYGNGPGYKVVGGERENVSMVDYA 420
421 HNNYQAQSAVPLRHETHGGEDVAVFSKGPMAHLLHGVHEQNYVPHVMAYAACIGANLGHC 480
481 APASSAGSLAAGPLLLALALYPLSVLF 507
```

Fig. 10 continued

Secretable ALPI with Crown-Domain of PLAP (chimera)

```
  1 VIPAEEENPAFWNRQAAEALDAAKKLQPIQKVAKNLILFLGDGLGVPTVTATRILKGQKN  60
 61 GKLGPETPLAMDRFPYLALSKTYNVDRQVPDSAATATAYLCGVKANFQTIGLSAAARFNQ 120
121 CNTTRGNEVISVMNRAKQAGKSVGVVTTTRVQHASPAGTYAHTVNRNWYSDADMPASARQ 180
181 EGCQDIATQLISNMDIDVILGGGRKYMFPMGTPDPEYPADASQNGIRLDGKNLVQEWLAK 240
241 HQGAWYVWNRTELMQASLDQSVTHLMGLFEPGDTKYEIHRDPTLDPSLMEMTEAALRLLS 300
301 RNPRGFYLFVEGGRIDHGHHEGVAYQALTEAVMFDDAIERAGQLTSEEDTLTLVTADHSH 360
361 VFSFGGYPLRGSSIFGLAPGKARDRKAYTVLLYGNGPGYVLKDGARPDVTESESGSPEYR 420
421 QQSAVPLDEETHGGEDVAVFARGPQAHLVHGVQEQSFVAHVMAFAACLEPYTACDLAPPA 480
481 CTTD 484
```

Secretable ALPP with Crown-Domain of ALPI (chimera)

```
  1 IIPVEEENPDFWNREAAEALGAAKKLQPAQTAAKNLIIFLGDGMGVSTVTAARILKGQKK  60
 61 DKLGPEIPLAMDRFPYVALSKTYNVDKHVPDSGATATAYLCGVKGNFQTIGLSAAARFNQ 120
121 CNTTRGNEVISVMNRAKKAGKSVGVVTTTRVQHASPAGTYAHTVNRNWYSDADVPASARQ 180
181 EGCQDIATQLISNMDIDVILGGGRKYMFRMGTPDPEYPDDYSQGGTRLDGKNLVQEWLAK 240
241 RQGARYVWNRTELMQASLDPSVTHLMGLFEPGDMKYEIHRDSTLDPSLMEMTEAALRLLS 300
301 RNPRGFFLFVEGGRIDHGHHESRAYRALTETIMFDDAIERAGQLTSEEDTLSLVTADHSH 360
361 VFSFGGYTLRGSSIFGLAPSKAQDSKAYTSILYGNGPGYVFNSGVRPDVNESESGSPDYQ 420
421 QQAAVPLSSETHAGEDVAVFARGPQAHLVHGVQEQTFIAHVMAFAACLEPYTACDLAPPA 480
481 GTTD 484
```

USE OF ALKALINE PHOSPHATASE IN THE TREATMENT OF REDUCED RENAL FUNCTION

The invention relates to the field of medicine and in particular to the use of alkaline phosphatase in the treatment of renal diseases, such as reduced renal function. The present invention also relates to the field of pharmacy and in particular to the pharmaceutical use of alkaline phosphatase.

There are multiple renal diseases that can result in a reduced renal function. Acute Renal Failure (ARF) is one of the renal disorders that result in a reduced renal function. Without limiting the scope of the invention, ARF is discussed in more detail.

Acute renal failure (ARF) is defined as an acute loss of kidney function that results in an increase of the serum creatinine level.

The annual incidence of community-acquired ARF is approximately 100 cases per 1 million population, and it is diagnosed in only 1% of hospital admissions at presentation. On the other hand, hospital-acquired ARF occurs in as many as 4% of hospital admissions and 20% of critical care admissions. This increased incidence of hospital-acquired ARF is multifactorial: it is related to an aging population with increased risks of ARF, the high prevalence of nephrotoxic exposures possible in a hospital setting, and increasing severity of illness.

Over the past 40 years, the survival rate for acute renal failure has not improved, primarily because affected patients are now older and have more comorbid conditions. Depending on the severity of renal failure, the mortality rate can range from 7 percent to as high as 80 percent.

In acute renal failure, the glomerular filtration rate decreases over days to weeks. As a result, excretion of nitrogenous waste is reduced, and fluid and electrolyte balances cannot be maintained. Patients with acute renal failure are often asymptomatic, and the condition is diagnosed by observed elevations of blood urea nitrogen (BUN) and serum creatinine levels. Complete renal shutdown is present when the serum creatinine level rises by at least 0.5 mg per dL per day (which equals 44 µmol per L per day) and the urine output is less than 400 mL per day (oliguria).

Pathophysiology:
The driving force for glomerular filtration is the pressure gradient from the glomerulus to the Bowman space. Glomerular pressure is primarily dependent on renal blood flow (RBF) and is controlled by combined resistances of renal afferent and efferent arterioles. Regardless of the cause of ARF, reductions in RBF represent a common pathologic pathway for decreasing glomerulo filtration rate (GFR). The etiology of ARF comprises 3 main mechanisms.

Prerenal failure is defined by conditions with normal tubular and glomerular function. In prerenal acute renal failure, the problem is impaired renal blood flow as a result of true intravascular depletion, decreased effective circulating volume to the kidneys or agents that impair renal blood flow as a result GFR is depressed Intrinsic acute renal failure is subdivided into four categories: tubular disease, glomerular disease, vascular disease and interstitial disease. In intrinsic acute renal failure, the renal parenchyma is injured.

Postobstructive renal failure initially causes an increase in tubular pressure, decreasing the filtration driving force. Postrenal acute renal failure can only occur if both urinary outflow tracts are obstructed or the outflow tract of a solitary kidney is obstructed. The condition is most often due to obstruction of the lower urinary tract.

Prerenal Failure
The primary agents that cause prerenal acute renal failure are angiotensin-converting enzyme (ACE) inhibitors and nonsteroidal anti-inflammatory drugs (NSAIDs). The inhibition of ACE prevents the conversion of angiotensin I to angiotensin II, leading to decreased levels of angiotensin II. Angiotensin II increases the glomerular filtration rate by causing constriction of the efferent arteriole; its absence decreases the glomerular filtration rate because of dilatation of the efferent arteriole.

Intrinsic Acute Renal Failure
Tubular Disease
Acute tubular necrosis through depressed RBF is the most common cause of intrinsic acute renal failure in hospitalized patients. Diminished renal blood flow causes ischemia in the renal parenchyma. If the ischemia is prolonged, acute tubular necrosis may develop. This initial ischemic insult triggers production of oxygen free radicals and enzymes that continue to cause cell injury even after restoration of RBF. Tubular cellular damage results in disruption of tight junctions between cells, allowing back-leak of glomerular filtrate and further depressing effective GFR. In addition, dying cells slough off into the tubules, forming obstructing casts, which further decrease GFR and lead to oliguria. Ischemic acute tubular necrosis is frequently reversible, but if the ischemia is severe enough to cause cortical necrosis, irreversible renal failure can occur.

Acute tubular necrosis has three phases. Renal injury evolves during the initiation phase, which lasts hours to days. In the maintenance phase, which lasts days to weeks, the glomerular filtration rate reaches its nadir and urine output is at its lowest. The recovery phase lasts days, often beginning with postacute tubular necrosis diuresis. Hypovolemia from excess urine output is a concern during this phase. Despite recovery of urine production, patients can still have difficulty with uremia and homeostasis of electrolytes and acid because tubular function is not completely recovered.

Glomerular Disease
Most common glomerular disease that leads to ARF is glomerulonephritis. Glomerulonephritis is characterized by hypertension, proteinuria and hematuria. Of the many types of glomerulonephritis, most are associated with chronic renal disease. In general, the two types of glomerulonephritis that cause acute renal failure are rapidly progressive glomerulonephritis and acute proliferative glomerulonephritis. The latter type occurs in patients with bacterial endocarditis or other postinfectious conditions.

Vascular Disease
Microvascular or macrovascular disease (major renal artery occlusion or severe abdominal aortic disease) can cause acute renal failure.

Interstitial Disease
Acute interstitial nephritis usually presents with fever, rash and eosinophilia. Urine staining that is positive for eosinophils is suggestive of this condition. Acute interstitial nephritis is usually the result of an allergic reaction to a drug, but it may also be caused by autoimmune disease, infection or infiltrative disease.

Recovery from ARF is first dependent upon restoration of RBF. Early RBF normalization predicts better prognosis for recovery of renal function. In prerenal failure, restoration of circulating blood volume is usually sufficient. Rapid relief of urinary obstruction in postrenal failure results in a prompt decrease of vasoconstriction. With intrinsic renal failure, restoration of blood volume alone does not restore the kidney function. Removal of tubular toxins and initiation of therapy for glomerular or tubular diseases decrease renal afferent vasoconstriction and may reverse ARF. Initial treatment should focus on correcting fluid and electrolyte balances and uremia while the cause of acute renal failure is being sought. A volume-depleted patient is resuscitated with saline. More often, however, volume overload is present, especially if patients are oliguric or anuric.

One example of a current treatment is intravenous administered Furosemide (Lasix). Another example of one of the current treatments is intravenously administered calcium. Potassium can be temporarily shifted into the intracellular compartment using intravenously administered insulin (10 units) and glucose (25 g), inhaled beta agonists or intravenously administered sodium bicarbonate. Potassium excretion is achieved with sodium polystyrene sulfonate (Kayexalate) and/or diuretics. Sodium polystyrene sulfonate is given orally (25 to 50 g mixed with 100 mL of 20 percent sorbitol) or as an enema (50 g in 50 mL of 70 percent sorbitol and 150 mL of tap water). If these measures do not control the potassium level, dialysis is initiated.

Acidosis is typically treated with intravenously or orally administered sodium bicarbonate if the serum bicarbonate level is less than 15 mEq per L (15 mmol per L) or the pH is less than 7.2. Patients can also be treated orally with sodium bicarbonate tablets, Shohl's solution in 30-mL doses or powdered sodium bicarbonate. Serum bicarbonate levels and pH should be followed closely. Intractable acidosis requires dialysis.

All medications should be reviewed, and their dosages should be adjusted based on the glomerular filtration rate and the serum levels of medications.

Between 20 and 60 percent of patients require short-term dialysis, particularly when the BUN exceeds 100 mg per dL (35.7 mmol per L of urea) and the serum creatinine level exceeds the range of 5 to 10 mg per dL (442 to 884 µmol per L). Indications for dialysis include acidosis or electrolyte disturbances that do not respond to pharmacologic therapy, fluid overload that does not respond to diuretics, and uremia. In patients with progressive acute renal failure, urgent consultation with a nephrologist is indicated.

Some of the above-mentioned treatments result in a (partly) restored kidney function. Other treatment results in improved function when compared to non-treated persons. However, there is still a need for alternative treatments.

The goal of the present invention is to provide an alternative treatment to improve renal function, especially in cases where the renal function is at least partly impaired/reduced. The present invention provides an alternative treatment using alkaline phosphatase to improve a situation in which the renal function is reduced.

In a first embodiment, the invention provides use of alkaline phosphatase (AP) in the manufacture of a medicament for improving reduced renal function.

The term "improving" includes slowing down the reduction, stopping the reduction or at least partly reversing the reduction of the renal function.

The term "reduced renal function" is typically used to refer to a situation in which the renal function is reduced by comparing the value of at least one renal related parameter to a recognised or average (laboratory) value of said parameter. If for example the amount of protein in the urine of a subject (preferably a human being) is (significantly) above a recognised or average (laboratory) value, said person is said to have a "reduced renal function". The corresponding analysis can be performed in a laboratory but also in a home setting. For example, since September 2006 the Dutch "Nierstichting" has introduced a simple test (named Niercheck) which can be performed at home to test whether the kidneys function properly. This test is directed to the amount of protein in the urine.

Other examples of parameters that can be tested are glomerular filtration rate (GFR), serum creatinine levels, electrolyte derangement, amount of produced urine, blood urea nitrogen (BUN), calcium, phosphorous, albumin levels, or red and white blood cells in urine. Other tests that can be performed are a complete blood count with differential. Preferably, all possible patients have the following urine studies: dipstick test, microscopy, sodium and creatinine levels, and urine osmolality determination.

As disclosed herein within the experimental part it is also possible to analyse a urine sample on the presence of absence of RNA molecule. Preferably, said RNA molecule is a mRNA molecule. Even more preferred said mRNA molecule is iNOS mRNA. In a most preferred embodiment said RNA is obtained from urine-secreted renal cells.

Based on the above described analysis, it is determined whether or not a subject (preferably a human being) is suffering from a reduced renal function. A decreased GFR or an elevated serum creatinine level or a reduced amount of produced urine or any combination thereof are for example (a) strong indication(s) that the tested subject needs treatment as described herein.

The use as described herein can thus be preceded by an analysis step which for example comprises taking a sample from a subject that is suspected to suffer from reduced renal function and analysing said sample for any of the above given parameters (or a combination thereof) and comparing the obtained result(s) with average or recognised values. Examples of suitable samples are a urine sample or a blood sample. Analysis on urine and/or blood samples can further be accompanied by renal ultrasound examination. In a preferred embodiment, the analysis is performed by or under the responsibility of a physician. As soon it is clear that the renal function is decreased, treatment according to the invention is started.

A reduced renal function can be the result of different disorders. Many cases of impaired renal function result in mild, asymptomatic illness that is not recognised by the patient, is not brought to medical attention, and remains undiagnosed. The incidence and prevalence of such mild episodes of impaired renal function are unknown but are considered to be substantial. However, such mild malfunctioning can evolve into serious problems and hence early treatment (for example as described herein) is important.

In a preferred embodiment, the invention provides use of alkaline phosphatase (AP) in the manufacture of a medicament for improving reduced renal function, wherein said renal function is reduced due to renal failure. Renal failure is the condition in which the kidneys fail to function properly. Physiologically, renal failure is described as a decrease in the glomerular filtration rate. Clinically, this manifests in an elevated serum creatinine. It can broadly be divided into two categories: acute renal failure and chronic renal failure.

Chronic renal failure (CRF) develops slowly and gives few symptoms initially. It can be the complication of a large number of kidney diseases, such as, glomerulonephritis, chronic pyelonephritis and urinary retention. End-stage renal failure (ESRF) is the ultimate consequence, in which case dialysis is generally required until a donor for a renal transplant is found. In acute renal failure the function of the kidney is almost completely abolished. In a preferred embodiment said renal failure is acute renal failure.

Acute renal failure (ARF) is, as the name implies, a rapidly progressive loss of renal function, generally characterised by oliguria (decreased urine production, quantified as less than 400 mL per day in adults, less than 0.5 mL/kg/h in children or less than 1 mL/kg/h in infants), body water and body fluids disturbances and electrolyte derangement. Patients suffering from acute renal failure are typically hospitalised due to the seriousness of their condition. At present, an underlying cause must be identified to arrest the progress, and dialysis may be necessary to bridge the time gap required for treating these fundamental causes. Based on the present invention, therapy with alkaline phosphatase can immediately be started even without knowing the underlying cause and without loosing precious time. In a preferred embodiment, the invention provides the use of alkaline phosphatase (AP) in the manufacture of a medicament for improving reduced renal function, wherein said reduced renal function is induced or sustained or exacerbated due to renal failure and wherein renal failure is acute renal failure, i.e. in a preferred embodiment, the invention provides the use of alkaline phosphatase (AP) in the manufacture of a medicament for treating reduced renal function induced or sustained or exacerbated by acute renal failure (ARF).

Acute renal failure can be present on top of chronic renal failure. This is called acute-on-chronic renal failure (AoCRF). The acute part of AoCRF may be reversible and the aim of treatment is to return the patient to their baseline renal function, which is typically measured by serum creatinine. In yet another embodiment, the invention therefore provides use of alkaline phosphatase (AP) in the manufacture of a medicament for improving reduced renal function, wherein said renal function is (further) reduced due to acute-on-chronic renal failure.

In yet another preferred embodiment, the reduced renal function is reversible, i.e. the renal function can be at least somewhat improved by treatment according to the invention.

As outlined in detail by Agrawal and Swartz (American Family Physician, Apr. 1, 2000 volume 61, no 7; cover story), the cause of acute renal failure can be determined by using a step-by-step approach. Based on this article the skilled person is very well capable of subdividing patients into any of the 3 ARF categories, i.e. to determine whether a patient suffers from prerenal ARF, intrinsic ARF or postrenal ARF.

For example, the diagnosis intrinsic ARF is typically determined upon suggestive history and physical findings, fractional excretion of sodium of greater than 3%, urine osmolality of 250 to 300 mOsm, active urine sediment. In intrinsic acute ARF, the renal parenchyma is injured. The damage to tubule cells leads to certain urine microscope findings. Parenchymal injury causes impaired sodium reabsorption and results in the above described parameters such as a fractional excretion of sodium of greater than 3 percent and an isotonic urine osmolality of 250 to 300 mOsm. Intrinsic acute renal failure is subdivided into 4 categories: tubular disease, glomerular disease, vascular disease and interstitial disease.

Acute tubular necrosis is the most common cause of intrinsic acute renal failure in hospitalized patients. This condition is usually induced by ischemia or toxins. In ischemic acute tubular necrosis, unlike prerenal acute renal failure, the glomerular filtration rate does not improve with the restoration of renal blood flow. Ischemic acute tubular necrosis is frequently reversible, but if the ischemia is severe enough to cause cortical necrosis, irreversible renal failure can occur. Contrast agents and antibiotics, especially aminoglycosides are the agents most often associated with acute tubular necrosis. The condition can also be caused by pigment from myoglobinuria (rhabdomyolysis) or hemoglobinuria (hemolysis). Acute tubular necrosis has three phases. Renal injury evolves during the initiation phase, which lasts hours to days. In the maintenance phase, which lasts days to weeks, the glomerular filtration rate reaches its nadir and urine output is at its lowest. The recovery phase lasts days, often beginning with postacute tubular necrosis diuresis. Hypovolemia from excess urine output is a concern during this phase. Despite recovery of urine production, patients can still have difficulty with uremia and homeostasis of electrolytes and acid because tubular function is not completely recovered. Diligent monitoring is indicated throughout all phases of acute tubular necrosis. Patients at risk for acute tubular necrosis include those with diabetes, congestive heart failure or chronic renal insufficiency. Acute tubular necrosis may be prevented by promptly treating patients with reversible causes of ischemic or prerenal acute renal failure and by maintaining appropriate hydration in patients who are receiving nephrotoxins. Once acute tubular necrosis develops, therapy is supportive. Drugs such as mannitol, loop diuretics, dopamine and calcium channel blockers have been somewhat successful in promoting diuresis in animals, but similar results have not been obtained in humans.

In a preferred embodiment, the invention provides use of alkaline phosphatase (AP) in the manufacture of a medicament for improving reduced renal function, wherein said renal function is reduced due to renal failure, preferably acute renal failure and wherein said reduced renal function is induced or sustained or exacerbated by intrinsic acute renal failure, preferably acute tubular necrosis. I.e. the invention also provides use of alkaline phosphatase (AP) in the manufacture of a medicament for treating acute tubular necrosis.

Glomerulonephritis is characterized by hypertension, proteinuria and hematuria. Glomerulonephritis is typically described as an inflammation of the glomeruli. Of the many types of glomerulonephritis, most are associated with chronic renal disease. In general, the two types of glomerulonephritis that cause acute renal failure are rapidly progressive glomerulonephritis and acute proliferative glomerulonephritis. The latter type occurs in patients with bacterial endocarditis, or other postinfectious conditions. Rapidly progressive glomerulonephritis can be a primary disorder, or it can occur secondary to systemic disease. Once this condition is suspected, treatable systemic disease must be sought through serologic markers or renal biopsy. Renal function can decline quickly in patients with rapidly progressive glomerulonephritis, and end-stage renal disease can develop in days to weeks. Patients with rapidly progressive glomerulonephritis are usually treated with glucocorticoids and cyclophosphamide (Cytoxan). Plasma exchange is believed to benefit patients with Goodpasture's syndrome but has not been of proven benefit in patients with other types of glomerulonephritis.

Also this type of ARF can be treated by using alkaline phosphatase and hence, in a preferred embodiment, the invention provides use of alkaline phosphatase (AP) in the manufacture of a medicament for improving reduced renal function, wherein said renal function is reduced due to renal failure, preferably acute renal failure and wherein reduced renal function is induced or sustained or exacerbated by intrinsic acute renal failure, preferably glomerulonephritis. I.e. the invention also provides use of alkaline phosphatase (AP) in the manufacture of a medicament for treating glomerulonephritis.

Renal failure in general and acute renal failure in specific can evolve by different underlying causalities or in the course of different diseases such as ischemia, contrast agent pigments, systemic lupus erythematosus, small-vessel vasculitis, Henoch-Schönlein purpura, Goodpasture's syndrome, encarditis, poststreptococcal infection, postpneumococcal infection, diabetis, hypertension, atherosclerosis or cancer. Also the use of certain anti-microbial agents (such as Amphotericin B, caspofungin, vancomycin, levofloxacin, and aminoglycosides such as tobramycin and gentamicin), other drugs (e.g. chemotherapeutic agents (such as cisplatin, carboplatin, methotrexate), protease inhibitors (such as indinavir and ritonavir), gold, lithium, anti-inflammatory drugs (such as non-steroidal anti-inflammatory drugs, cyclosporin, tacrolimus, sirolimus), blood pressure medicaments (such as angiotensin converting enzyme (ACE) inhibitors and angiotensin receptor blockers (ARBs)) and certain chemicals (such as silicates, hydrocarbons, heavy metals (such as Cd, Hg, Pb), insecticides, herbicides, ethylene glycol and bacterial toxins (such as tetanus, streptococcal toxins)) are known to result in reduced renal function in subjects who have taken or have been exposed to said agents or chemicals.

The present invention can be used to treat reduced renal function induced or sustained or exacerbated by any of the above mentioned causalities. Hence, in a preferred embodiment, the invention provides use of alkaline phosphatase (AP) in the manufacture of a medicament for improving reduced renal function, wherein said reduced renal function is induced or sustained or exacerbated due to a medicament, drug and/or toxin, preferably selected from the group consisting of antibiotics, protease inhibitors, chemotherapeutic agents, anti-inflammatory agents, blood pressure medicaments, insecticides, herbicides, ethylene glycol, contrast dyes, heavy metals and bacterial toxins.

In yet another preferred embodiment, the invention provides use of alkaline phosphatase (AP) in the manufacture of a medicament for improving reduced renal function, wherein the obtained improvement of renal function is not a result of LPS detoxification by AP.

In an even more preferred embodiment, the invention provides use of alkaline phosphatase (AP) in the manufacture of a medicament for improving reduced renal function, wherein said reduced renal function is induced or sustained or exacerbated by decreased renal blood flow and/or ischemia. Said decreased renal blood flow and/or ischemia is preferably induced or sustained or exacerbated due to dehydration, heart failure, septic shock, severe blood loss, hypertension, atherosclerosis, and/or thrombosis.

In yet another preferred embodiment, the invention provides use of alkaline phosphatase (AP) in the manufacture of a medicament for improving reduced renal function, wherein said reduced renal function is induced or sustained or exacerbated by decreased renal blood flow and/or ischemia, wherein said reduced renal blood flow and/or ischemia is preferably induced or sustained or exacerbated due to a medicament or drug or toxin, preferably selected from the group consisting of anti-inflammatory agents (most preferably non-steroidal anti-inflammatory drugs) and blood pressure medicaments (most preferably angiotensin converting enzyme (ACE) inhibitors and/or angiotensin receptor blockers (ARBs)

The invention further provides use of alkaline phosphatase (AP) in the manufacture of a medicament for treating or preventing reduced renal function resulting from increased (renal) inducible NO synthase (iNOS) expression. Such a treatment is very useful in the treatment of so-called early renal damage/failure and can thus for example be used to treat or prevent early nephropathy. Persons in need of such a treatment are easily identified by determining the amount of iNOS and comparing the obtained value with an average level. By administering an effective amount of alkaline phosphatase to a person diagnosed with early renal damage/failure, the amount of renal iNOS is reduced. The present inventors have determined that treatment with alkaline phosphatase resulted in an attenuation of the increased expression of iNOS mRNA in kidney cells, resulting in reduced urinary excretion of NO metabolites. Treatment with AP ameliorates inflammatory responses, resulting in a reduced induction of renal iNOS expression, which leads to an attenuated production of NO metabolites and less proximal tubular damage.

Renal failure is usually accompanied with structural damage of renal cells that are secreted in the urine. Isolation of these cells from a urine sample and subsequent analysis of the RNA synthesis provides a useful monitoring tool for the kidney function, kidney damage and eventually reversion of the damage. In example 1 the expression of inducible nitric oxide synthase (iNOS) mRNA in the urine secreted renal cells is used as a marker for renal failure and could therefore be used to monitor the damage and reversion of the damage due to treatment with AP. Underlying mechanism of damage is the induction of reactive oxide species (ROS) by iNOS, leading to leakage of the kidney. Reduction of ROS induction through iNOS down regulation can be monitored by using this method.

In yet another embodiment, the invention therefore provides use of AP in the preparation of a medicament for improving reduced renal function, further comprising analyzing a urine sample for the presence or absence of an RNA molecule. Preferably, said RNA molecule is an mRNA molecule. Even more preferred said mRNA molecule is iNOS mRNA. In a most preferred embodiment said RNA is obtained from urine-secreted renal cells.

The invention uses alkaline phosphatase (AP) to improve a reduced (or impaired) renal function.

Alkaline phosphatase (AP); EC 3.1.3.1 according to IUBMB Enzyme Nomenclature, the common name is alkaline phosphatase (AP), an enzyme that catalyzes the reaction of a phosphatase monoester and $H_2O$ to an alcohol and phosphate. Other name(s) for AP are alkaline phosphomonoesterase; phosphomonoesterase; glycerophosphatase; alkaline phosphohydrolase; alkaline phenyl phosphatase; orthophosphoric-monoester phosphohydrolase (alkaline optimum). The systemic name of AP is phosphate-monoester phosphohydrolase (alkaline optimum).

AP is a wide specificity enzyme, it also catalyses transphosphorylations. In humans and other mammals at least four distinct but related alkaline phosphatase are known. They are intestinal, placental, placental-like, and liver/bone/kidney (or tissue non-specific) alkaline phosphatase. The first three are located together on chromosome 2 while the tissue non-specific form is located on chromosome 1. The exact physiological functions of the APs are not known, but AP appears to be involved in a large number of physiological processes.

A source of AP can be a commercial AP enzyme, or any composition comprising the AP enzyme and any means which is capable of producing a functional AP enzyme in the context of the current invention, such as DNA or RNA nucleic acids encoding an AP protein. The nucleic acid encoding AP may be embedded in suitable vectors such as plasmids, phagemids, phages, (retro)viruses, transposons, gene therapy vectors and other vectors capable of inducing or conferring production of AP. Also native or recombinant micro-organisms, such as bacteria, fungi, protozoa and yeast may be applied as a source of AP in the context of the current invention.

AP containing compositions for use according to the current invention preferably comprise an eukaryotic AP, more preferably a mammalian AP, which may be of the types tissue non-specific AP, such as liver-bone or kidney type, or tissue specific such as placental AP, intestinal AP and placental-like AP. The latter, also known as germ cell AP, is localized to testis, thymus and certain germ cell tumors (1), and is closely related to both the placental and intestinal forms of alkaline phosphatase (2). The skilled person is very well capable of searching nucleic acid libraries and selecting a sequence that encodes alkaline phosphatase. Most preferably the mammalian AP is a human or a bovine AP. Hence, in a preferred embodiment, the invention provides use of alkaline phosphatase (AP) in the manufacture of a medicament for improving reduced renal function, wherein said AP is mammalian AP and even more preferably wherein said AP is human AP. Non-limiting examples of a human AP sequence can be found in the NCBI (Genpept) collection and include: NP_001622 (intestinal AP), NP_001623 (placental AP), NP_112603 (placental-like AP) or NP_000469 (tissue non-specific AP). The invention also comprises the use of a polymorphism of any of said sequence. In yet another preferred embodiment, said AP is placental AP, placental-like AP, intestinal AP or liver/bone/kidney AP.

In yet another preferred embodiment, the invention provides use of AP in the preparation of a medicament for improving reduced renal function, wherein said AP is recombinant AP.

From a conformational point of view, an alkaline phosphatase roughly consists of two domains: a crown domain and an active-site domain. The active-site domain can be divided in separate parts like the catalytic residue and the three metal ion sites (Zn1, Zn2 and Mg3). From a primary structure point of view it is clear that the crown domain is flanked by the amino acids that form the active site domain. The amino acid sequence of alkaline phosphatases and the relative positions of the catalytic and crown domain are known by the skilled person. As an example, reference is made to FIG. 10 which shows, amongst others, the amino acid sequence of the four human alkaline phosphatases. The crown domain is underlined in these sequences.

Alkaline phosphatases are present in virtually all organisms from bacteria to humans. In a preferred embodiment, a method according to the invention is provided, wherein AP is an isolated or recombinant alkaline phosphatase comprising a crown domain and a catalytic domain, wherein said crown domain and said catalytic domain are obtained from different alkaline phosphatases and wherein at least one of said different phosphatases is a human phosphatase. The other phosphatase is for example ECAP (*Escherichia coli* alkaline phosphatase) or one of the seven known BIAPs (Bovine Intestinal Alkaline Phosphatase). In a preferred embodiment, an isolated or recombinant alkaline phosphatase comprising a crown domain and a catalytic domain, wherein said crown domain and said catalytic domain are obtained from different alkaline phosphatases and wherein the different alkaline phosphatases are human phosphatases is used. This is especially useful if the modified phosphatase is subsequently used in human therapy. It is expected that such (genetically) modified phosphatases of human origin are not or very little immunogenic. However it is clear to the skilled person that if a modified phosphatase is for example used in "in vitro" or "ex vivo" diagnostics a modified phosphatase may well be composed of for example a human and an *E. coli* alkaline phosphatase or may be composed of a bovine and an *E. coli* alkaline phosphatase.

In yet another preferred embodiment, a method according to the invention is provided, wherein AP is an isolated or recombinant alkaline phosphatase comprising a crown domain and a catalytic domain, wherein said crown domain and said catalytic domain are obtained from different alkaline phosphatases and wherein said crown domain is the crown domain of placental AP (ALPP) and wherein said catalytic domain is the catalytic domain of intestinal AP (ALPI). Preferably, at least one of said different phosphatases is a human phosphatase and in an even more preferred embodiment, both different phosphatases are human phosphatases.

Other preferred domain swapped mutants that are based on the human alkaline phosphatases are:

| Catalytic domain | Crown domain | Referred to as |
|---|---|---|
| ALPI | GCAP | catALPI/crownGCAP |
|  | TNAP | catALPI/crownTNAP |
| ALPP | GCAP | catALPP/crownGCAP |
|  | TNAP | catALPP/crownTNAP |
| GCAP | ALPI | catGCAP/crownALPI |
|  | ALPP | catGCAP/crownALPP |
|  | TNAP | catGCAP/crownTNAP |
| TNAP | ALPI | catTNAP/crownALPI |
|  | ALPP | catTNAP/crownALPP |
|  | GCAP | catTNAP/crownGCAP |

For the sake of clarity, ALPI is intestinal AP, ALPP is placental AP, GCAP is placental-like AP and TNAP is tissue non-specific AP.

It is clear that also combinations between the catalytic domain of ECAP or any of the human forms (ALPI, ALPP, GCAP or TNAP) with the crown domain of BIAP can be made. Moreover, combinations of the crown domain of BIAP with the catalytic domain of ECAP or any of the human forms can also be produced.

Another class of useful modified phosphatases are phosphatases which under natural conditions are linked to the membrane of a cell via a glycosylphosphatidylinositol (GPI) anchor but which are now modified such that they are no longer attached to the membrane of a cell. Examples of phosphatases that are GPI-anchored are alkaline phosphatase and 5'-nucleotidase. All isoenzymes are functionally active in the cell membrane and GPI-anchor deficient forms are not naturally present at detectable levels. Although serum alkaline phosphate activity has been demonstrated it is generally accepted that the enzyme is still present in shed membrane fractions or membrane vesicles. AP activity in milk is also present in fractions containing membrane vesicles. The GPI anchor is stored as a precursor molecule in the cell where it is attached to the attachment site through a transamidase. The backbone of the GPI-anchor is identical in mammals, but cell-type dependent modifications are known.

Alkaline phosphatases are predominantly found in association with plasma-membranes via their GPI anchor. For example, neutrophils present the enzyme against the background of their negatively charged cell membrane instead of releasing it into the inflammatory microenvironment. For this reason it was commonly accepted before the present invention that for optimal in vivo activity of AP the enzyme should be embedded in a cell membrane or a vesicular membrane.

For pharmaceutical use of AP in human subjects it is for most applications preferred to apply human forms of the enzyme for medicaments and treatment, as AP forms obtained from other species may be immunogenic in human subjects and treatment could elicit immunological reactions and pathological side effects. In some subjects even lethal side effects i.e. anaphylactic shock (shown in our animal studies) may occur and the risks of immunological side effects are therefore preferably minimized. As isolation of AP from humans is practically not feasible, human recombinant forms of the AP proteins can be routinely produced in different recombinant expression platforms. However, expression and purification of GPI modified and membrane-anchored proteins is notoriously difficult; GPI proteins are difficult to separate from membranes and difficult to isolate and purify. However, before the present invention, the GPI anchor and membrane localisation have always been regarded as essential for the biological activity of AP.

In one of the embodiments of the present invention, however, a method according to the invention is provided, wherein AP is an isolated or recombinant phosphatase comprising a modification in the glycosylphosphatidylinositol (GPI) signal sequence, wherein said modification results in a secreted phosphatase, i.e. the phosphatase is not attached to the cell membrane.

In a preferred embodiment, an isolated or recombinant phosphatase comprising a modification in the glycosylphosphatidylinositol (GPI) signal sequence, wherein said modification results in a secreted phosphatase that is biological active, i.e. it shows activity towards a biological (relevant) substrate, is used.

There is no general sequence responsible for the attachment of a GPI anchor, but there is a clear consensus:
1) hydrophobic stretch of amino acids at the C-terminus (at least 11 amino acids, but preferably more than 11 amino acids)
2) Upstream of the hydrophobic region, a spacer of hydrophylic amino acids (5-12 amino acids)
3) GPI is attached to a small amino acid: glycine, aspartic acid, asparagine, alanine, serine or cysteine.
4) The 2 subsequent Amino acids downstream of the GPI attachment site must be small amino acids and in the majority of cases they are selected from glycine, aspartic acid, asparagine, alanine, serine or cysteine.

Based on this consensus, the skilled person is capable of mutating this consensus, for example by inserting one or multiple amino acids and disrupting part of the consensus. However in a preferred embodiment, an isolated or recombinant phosphatase comprising a modification in the glycosylphosphatidylinositol (GPI) signal sequence, wherein said modification results in a secreted phosphatase and wherein said modification comprises a mutation or a deletion of the amino acid sequence encompassing the consensus GPI signal sequence is used.

For applications in human therapy A is desired that the resultant modified phosphatase is not or very little immunogenic, i.e. that the modified phosphatase is essentially of human origin. In a preferred embodiment, a method according to the invention is provided, wherein AP is an isolated or recombinant phosphatase comprising a modification in the glycosylphosphatidylinositol (GPI) signal sequence, wherein said modification results in a secreted phosphatase (preferably with activity against a biological relevant substrate) and wherein said phosphatase is a human phosphatase.

Examples of phosphatases that are GPI-anchored are alkaline phosphatase and 5'-nucleotidase and hence in a preferred embodiment, an isolated or recombinant phosphatase is used, comprising a modification in the glycosylphosphatidylinositol (GPI) signal sequence, wherein said modification results in a secreted phosphatase and wherein said phosphatase is an alkaline phosphatase, for example a human alkaline phosphatase, such as for instance human liver-kidney-bone phosphatase, human intestinal alkaline phosphatase, or human placental-like alkaline phosphatise.

It is clear that any of the described secretable modified phosphatase can for example be produced by introducing into a host cell a nucleic acid capable of encoding said secretable phosphatase, preferably in operable linkage with regulatory sequences, and allowing said host cell to express said secretable phosphatase and optionally isolating the produced phosphatase from the medium in which the host cell are grown and/or maintained. However, apart from mutations in the above mentioned GPI-attachment sequence, other methods exist that make GPI-anchorless, secreted proteins:
1) After expression as membrane anchored proteins, phospholipases may be used to cleave off the GPI anchor.
2) Interference with the production of the GPI anchor or the use of a cell (type) that is deficient in GPI anchor production may also be used to make a secretable form of an otherwise GPI-anchored protein. Examples of cell lines that have been made to be deficient in GPI anchoring biochemistry are e.g. Jurkat, AM-B, C84, BW, S49, CHO and Raji.
3) Interference with or the use of a cell deficient in transamidases may be used to inhibit attachment of a GPI anchor to the protein, rendering the protein anchorless and secretable. Such a deficient cell has been obtained through mutagenesis in CHO.

It is clear to the skilled person that a modified phosphatase which comprises a crown domain and a catalytic domain, wherein said crown domain and said catalytic domain are obtained from different alkaline phosphatases can be further modified and made secretable. Hence, in a preferred embodiment, a method according to the invention is provided, wherein AP is an isolated or recombinant phosphatase comprising a modification in the glycosylphosphatidylinositol (GPI) signal sequence, wherein said modification results in a secreted phosphatase and wherein said recombinant phosphatase further comprises a crown domain and a catalytic domain that are obtained from different phosphatases. Non-limiting examples of such (alkaline) phosphatase mutants are provided in FIG. 10. Such a combined or "double" mutant results for example in a modified phosphatase with a certain specific activity, stability or substrate specificity and at the same time production of such a product is greatly enhanced by the fact that it can be isolated from the medium surrounding the producer cells.

The AP may be administered via different routes, for example intravenously, rectally, bronchially or orally.

In a preferred embodiment, the used route of administration is intravenously. It is clear for the skilled person, that preferably an effective amount of AP is delivered. As a startpoint 10-500 U/kg/day can be used. If the intravenous route of administration is used, AP (at least for a certain amount of time) is preferably applied via continuous infusion.

The current invention also provides compositions comprising a source of AP, amongst which are pharmaceutical and nutraceutical compositions comprising a source of AP. The compositions may optionally comprise pharmaceutically acceptable excipients, stabilizers, activators, carriers, permeators, propellants, desinfectants, diluents and preservatives. Suitable excipients are commonly known in the art of pharmaceutical formulation and may be readily found and applied by the skilled artisan, references for instance Remmington's Pharmaceutical Sciences, Mace Publishing Company, Philadelphia Pa., 17th ed. 1985. In a preferred embodiment the compositions comprising a source of AP are suitable for oral administration and comprise an enteric coating to protect the AP from the adverse effects of gastric juices and low pH. Enteric coating and controlled release formulations are well known in the art (references as described above). Enteric coating compositions in the art may comprise of a solution of a water-soluble enteric coating polymer mixed with the active ingredient(s) such as AP and other excipients, which are dispersed in an aqueous solution and which may subsequently be dried and/or pelleted. The enteric coating formed offers resistance to attack of AP by atmospheric moisture and oxygen during storage and by gastric fluids and low pH after ingestion, while being readily broken down under the alkaline conditions which exist in the lower intestinal tract.

In a preferred embodiment, a subject (preferably a human being) is provided with an effective amount of AP via any suitable route of administration and with the AP in any appropriate form. Preferably parameters indicative of renal function are determined before administration of AP and after administration of AP, allowing determining whether or not treatment is successful. Administration of further doses is repeated as often as necessary, preferably until the renal function parameters are considered to be acceptable. One example of a suitable parameter is the presence or absence of an RNA molecule. Preferably, said RNA molecule is an mRNA molecule. Even more preferred said mRNA molecule is iNOS mRNA. In a most preferred embodiment said RNA is obtained from urine-secreted renal cells.

Another preferred mode of admistration comprises the use of pharmaceutical compositions comprising sources of AP which may be delivered in a daily doses regime for a prolonged period of time. Preferably, the pharmaceutical compositions comprise an enteric coating to protect AP from the detrimental effects of gastric juices (pH 1.0 to 2.5) and ensure efficient delivery of AP.

In yet another embodiment, the use of AP in the preparation of a medicament for improving reduced renal function is combined with any other therapy (i.e. combinatorialy therapy). Such other therapy is for example also aiming at improving the renal function. Examples of other therapies aiming at improving the renal function are outlined above. Non-limiting examples are treatment with Furosemide (Lasix), calcium or dialysis. Other examples of suitable combination therapy are treatment with AP and at least one iNOS inhibitor or treatment with AP and at least one TNFα inhibitor. The active compounds can be administered sequentially or at the same time.

In yet another preferred embodiment, the invention provides a method for treating a subject (preferably a human) with reduced renal function comprising administering an effective amount of AP to a subject in need thereof. In a preferred embodiment, said renal function is reduced due to renal failure. Said method can further be extended by identification of a subject that suffers from reduced renal function. In a preferred embodiment, the invention provides a method for treating a subject (preferably a human) with reduced renal function comprising administering an effective amount of AP to a subject in need thereof, wherein the obtained improvement of renal function is not a result of LPS detoxification by AP.

One embodiment provides a method for treating a subject (preferably a human) with reduced renal function comprising administering an effective amount of AP to a subject in need thereof, wherein said reduced renal function is induced or sustained or exacerbated due to a medicament, drug and/or toxin. Said medicament, drug and/or toxin is preferably selected from the group consisting of antibiotics, protease inhibitors, chemotherapeutic agents, anti-inflammatory agents, blood pressure medicaments, insecticides, herbicides, ethylene glycol, contrast dyes, heavy metals and bacterial toxins.

Further provided is a method for treating a subject (preferably a human) with reduced renal function comprising administering an effective amount of AP to a subject in need thereof, wherein said reduced renal function is induced or sustained or exacerbated due to acute renal failure. Said reduced renal function is preferably induced or sustained or exacerbated by intrinsic acute renal failure. In one embodiment, said acute renal failure is induced or sustained or exacerbated by a medicament or a drug or a toxin, preferably selected from the group consisting of aminoglycosides, chemotherapeutic agents, contrast dyes, heavy metals and bacterial toxins.

Further provided is a method according to the invention, wherein said reduced renal function is induced or sustained or exacerbated due to intrinsic acute renal failure. Said intrinsic acute renal failure is preferably acute tubular necrosis and/or glomerulonephritis. Preferably, said acute tubular necrosis and/or glomerulonephritis is induced or sustained or exacerbated by a medicmanent or a drug or a toxin, most preferably selected from the group consisting of aminoglycosides, chemotherapeutic agents, contrast dyes, heavy metals and bacterial toxins.

Further provided is a method according to the invention, wherein said reduced renal function is induced or sustained or exacerbated by decreased renal blood flow and/or ischemia. Said decreased renal blood flow and/or ischemia is in one embodiment induced or sustained or exacerbated by dehydration, heart failure, septic shock, severe blood loss, hypertension, atherosclerosis and/or thrombosis. Preferably, said reduced renal blood flow and/or ischemia is induced or sustained or exacerbated by a medicament or drug or toxin, most preferably selected from the group consisting of angiotensin-converting enzyme (ACE) inhibitors and nonsteroidal anti-inflammatory drugs (NSAIDs).

Further provided is a method according to the invention, wherein said AP is a mammalian AP, preferably a human AP. More preferably the AP is placental AP, placental-like AP, intestinal AP or liver/bone/kidney AP. Most preferably, the AP is recombinant.

The invention will be explained in more detail in the following, non-limiting examples.

EXPERIMENTAL PART

Materials and Methods

Example 1

Effect of AP on Renal Function in Sepsis Patients

Patients

Fifteen patients admitted to the intensive care unit, diagnosed with reduced renal function were randomized to AP treatment (2 AP: 1 Placebo).

Arterial blood and catheterized urine were collected at several time points between 0 and 24 h after inclusion. Urine volumes were recorded and samples for the determination of NO metabolites were frozen at $-80°$ C. until assayed as described before (6). Creatinine and protein were determined by routine clinical chemistry.

Intervention

Bovine intestinal alkaline phosphatase (AP, AM-Pharma, Bunnik, The Netherlands) was derived from the intestinal mucosa of calf <6 months of age. Eligible patients received either AP or matching placebo (2.5 mM Tris-HCl, 1, 2.5 mM magnesium chloride, 0.05 mM zinc chloride, pH 7.3, with 40% glycerol as stabilizer) intravenously for 24 h in a 2:1 ratio. Patients randomized to AP received an initial bolus injection of 67.5 U/kg body weight administered over 10 minutes, followed by a continuous infusion of 132.5 U/kg during the remaining 23 h and 50 minutes.

Chemical Assays

The total amount of the stable NO metabolites, nitrate and nitrite, were determined as a measure of the production of NO radicals, using the Griess reaction, according to Moshage et al. (18). Heparinized plasma and urine samples were four-fold and forty-fold diluted with distilled water, respectively. The amounts of glutathione-S-transferase A1-1 (GSTA1-1) and GSTP1-1 in urine were determined to differentiate between proximal and distal tubular cell injury and were assayed in triplicate by ELISA as previously described (19; 20).

Determination of iNOS mRNA Expression

Urine samples were centrifuged at 700 g for 10 minutes at 4° C. RNA was isolated from cell pellets and reverse-transcribed into cDNA as described before (6). Human iNOS and GAPDH were amplified with a pre-developed Gene Expression Assay provided by Applied Biosystems (iNOS; Hs00167248_m1, GAPDH; Hs99999905_m1). All experiments were performed in triplicate. Sample quantities were normalized to the expression of the housekeeping gene, GAPDH.

Example 2

Effect of AP on Gentamicin Induced Renal Failure

Alkaline Phosphatase (AP) was evaluated for effects in a gentamicin-induced nephrotoxicity model in Wistar rats. The animals were provided with gentamicin at 120 mg/kg intramuscularly for seven consecutive days. Urine samples were collected over 24 hours on day 6 for measurements of urine volume, electrolytes ($Na^+$, $K^+$), creatinine, N-acetylglucosaminidase (NAG) and proteins. Blood samples were collected terminally at day 7; concentrations of serum creatinine, BUN and electrolytes ($Na^+$, $K^+$) were measured. The gentamicin-treated groups (n=8 per group) were provided with slow intravenous injection of vehicle or AP (100 U/kg), immediately before daily dosing of gentamicin, followed by another dosing every 12 hrs for seven consecutive days (total of 14 AP doses=1400 U/kg). A control group (n=8) received one intraperitoneal injection of physiological salt solution on day 0 and slow intravenous injections of vehicle using the same bi-daily dosing scheme as indicated for AP.

Example 3

Effect of AP on Cisplatin Induced Renal Failure

Alkaline phosphatase was evaluated for effects on kidney function in Wistar rats following a single intraperitoneal injection of Cisplatin at 7.5 mg/kg (denoted as day 0). Urine samples were collected over 24 hours on day 2 and day 5 for measurements of urine volume, electrolytes ($Na^+$, $K^+$), creatinine and proteins. Blood samples were collected on day 3 and day 6; concentrations of serum creatinine, BUN and electrolytes ($Na^+$, $K^+$) were measured. The cisplatin-treated groups (n=8 per group) are provided with slow intravenous injection of vehicle or AP (200 U/kg) 30 min before cisplatin challenge, followed by a second dosing 12 hours later; iv dosing will continue on day 1 (×2) and day 2 (×1) for a total of 5 doses (total AP dose of 1000 U/kg). A control group (n=8) received one intraperitoneal injection of physiological salt solution on day 0 and slow intravenous injections of vehicle using the same bi-daily dosing scheme as indicated for AP.

Example 4

Effect of AP on Sepsis Patients with Renal Failure

Patients

Thirty-six patients admitted to the intensive care units in of eight independent hospitals, diagnosed with sepsis were randomized to AP treatment (2 AP: 1 Placebo). Arterial blood and catheterized urine were collected at several time points between 0 and 48 h after inclusion. The verum and placebo treated groups were analyzed as whole or as subgroups limited to patients that presented with Renal Failure, defined as serum creatinine >150 gmol/L at baseline, or already on renal replacement therapy. Groups were analyzed for serum creatinine (by routine clinical chemistry), mortality, and need for renal replacement therapy.

Intervention

Bovine intestinal alkaline phosphatase (AP, AM-Pharma, Bunnik, The Netherlands) was derived from the intestinal mucosa of calf <6 months of age. Eligible patients received either AP or matching placebo (2.5 mM Tris-HCL, 2.5 mM magnesium chloride, 0.05 mM zinc chloride, pH 7.3, with 40% glycerol as stabilizer) intravenously for 24 h in a 2:1 ratio. Patients randomized to AP received an initial bolus injection of 67.5 U/kg body weight administered over 10 minutes, followed by a continuous infusion of 132.5 U/kg during the remaining 23 h and 50 minutes.

Other examples of suitable models that may be used to further show the efficacy of alkaline phosphatase in the treatment of reduced renal function are:

(1) Endotoxin-Induced Acute Renal Failure in Rats (J. Nephrol. 2005; 18: 374-381)

Acute renal failure can be induced in female Sprague-Dawley rats by intravenous injection of LPS (1 mg/kg from *E. coli* O111:B4, Sigma, Germany). This model is characterized by reduced Glomerular Filtration Rate, reduced blood pressure and increased NOx excretion.

(2) Anti-Thy-1.1 Model of Experimental Mesangial Proliferative Glomerulonephritis As described in Jefferson et al. (J. Nephrol. 1999; 12: 297-307), goat anti-rat thymocyte serum can be produced by repeated immunizations of a goat with lewis rat thymocytes ($2 \times 10^8$ cells per injection). Serum is collected after second and third injections, pooled, and an IgG enriched fraction obtained using a caprylic acid method. A single intravenous dose of 20 mg per 100 g body weight is then used to induce disease in 180-230 g male Wistar rats.

(3) Cadmium Induced Glomerulonephritis

Rats, intoxicated by daily i.p. injection for 5 days with 500 μg Cd2+ per kg per day and thereafter left untreated for 15 days show reduced Glomerular Filtration Rate as described in Jacquillet et al. (Am. J. Physiol. Renal Physiol. 2006; 290: 127-137).

In these experimental models, alkaline phosphatase will be administered through the intravenous route in order to prevent, slow down, stop or reverse the disease process. Alkaline phosphatase may be administered before disease induction, or early or late in disease establishment. Alkaline phosphatase may be administered only once or, during disease establishment, alkaline phosphatase may be administered multiple times or as a continuous infusion. Alkaline phosphatase will for example be administered in the dose range of 10 U/kg/day to 500 U/kg/day.

Efficacy parameters may be chosen from, but not limited to, the following: inflammatory parameters (infiltration, activation state of leucocytes and macrophages, cytokine production, complement activation), oxidative stress ($H_2O_2$ production, myeloperoxide content in the kidney, iNOS induction, NOx production, etc), kidney damage (dispostion of antibodies, coagulation, histology) and blood chemistry e.g. creatinine levels.

Results

Example 1

Effect of AP on Renal Function in Sepsis Patients

Patients

Fifteen patients (AP, n=10; placebo, n=5) with reduced renal function were randomized during a fifteen-month period.

AP attenuates Renal iNOS Induction

Q-PCR (or quantitative RT-PCR) was used to determine the levels of iNOS mRNA in cell pellets that were isolated from urine samples at baseline and at three separate time points in the first 24 h after intervention. The relative expression of iNOS in control healthy volunteers (n=4, data not shown) was normalized for the average cycle threshold ($C_T$) value of the housekeeping gene, GAPDH ($C_T$=23.6±0.3, delta $C_T$=12.1±0.1), and set to 1 as described before (6). iNOS expression was 42-fold induced in this patient group compared to controls, and AP-administration reduced this induction with 80±5% during the first 24 h. In contrast, placebo treated patients had a further increase in iNOS levels during the first 24 h after inclusion (840±85%, FIG. 1A), compared to baseline levels.

NO metabolites in blood were not significantly different between AP and placebo treated patients (data not shown). However, the urinary excretion of NO metabolites decreased with 80% [−85−−75] from 227 [166-531] at baseline to 41 [28-84] creatinine (P<0.05) after 24 h AP administration. After placebo treatment, the amount of urinary NO metabolites further increased with 70% [45-570] (from 81 [64-419] to 628 [65-1479] μmol/10 mmol creatinine, P<0.05). In addition, the cumulative urinary NO metabolites excretion was significantly lower in the AP treated patients (FIG. 1B).

AP Attenuates Kidney Damage

None of the patients required renal replacement therapy during the 28 days follow up period. All patients showed impaired renal function with mild proteinuria as shown in Table 1. The first 24 h, plasma creatinine clearance improved with 45% [30-180] in AP treated patients and deteriorated with 25% [−35−−15] in placebo treated patients as illustrated in Table 1. During the follow up period the median plasma creatinine levels declined significantly in AP treated patients, whereas no significant change in placebo treated patients was observed (Table 1).

The urinary excretion of both GSTA1-1 and GSTP1-1 was elevated in all patients, indicating proximal and distal tubule damage, respectively. During the first 24 h the amount of GSTA1-1 in urine of AP treated patients decreased with 70% [−80−−50] from 32.7 [11.5-131.1] to 6.5 [5.4-15.7] μg/10 mmol creatinine (P<0.05) compared to an increase with 200% [45-525] in placebo treated patients (from 26.9 [15.2-32.8] to 38.9 [33.0-205.8] P<0.05). The cumulative urinary GSTA1-1A excretion was significantly lower in AP treated patients (FIG. 1C). Furthermore, there was a trend towards an attenuated increase in urinary GSTP1-1 excretion (from 22.7 [13.6-41.3] at baseline to 11.9 [8.5-82.5] μg/10 mmol creatinine after 24 h, P=0.072) upon AP treatment. However, for the cumulative urinary GSTP1-1 excretion no significant differences were observed between the two treatment groups during the first 24 hours of the treatment (FIG. 1D).

Example 2

Effect of AP on Gentamicin Induced Renal Failure

Gentamicin at 120 mg/kg×7 caused severe renal impairment in rats as manifested by polyuria, proteinuria, reduced electrolyte excretion, increased $FE_{Na}$, enzymuria (NAG), elevation of serum creatinine and BUN, diminished creatinine clearance, a measure of glomerular filtration rate, and increased kidney weight.

Bi-daily AP injections for 7 days (100 U/kg bid×14), with the first dose given before daily administration of gentamicin, resulted in a reduction of serum creatinine (FIG. 2) and BUN levels (FIG. 3) as well as an increase in creatinine excretion in the urine (FIG. 4). These improvements are contributed to the increased creatinine clearance as a result of the treatment with AP (FIG. 5) In this example it is shown that AP, 100 U/kg IV bid×7 has protective effects against gentamicin-induced nephrotoxicity in rats, with regard to BUN, $S_{Cr}$, $C_{Cr}$, and $U_{cr}$.

Example 3

Effect of AP on Cisplatin Induced Renal Failure

Cisplatin 7.5 mg/kg i.p. caused reduced renal function as was reflected in the following parameters: polyuria, proteinuria, reduced electrolyte excretion, elevation of serum creatinine and BUN, and diminished creatinine clearance, a measure of glomerular filtration rate.

In this example it is shown that AP (200 U/kg×5 i.v.), protects against cisplatin-induced proteinuria in rats (FIG. 6), a measure of tubular damage in this model, and improves endogenous creatinine clearance.

Example 4

Effect of AP on Sepsis Patients with Renal Failure

Patients

Thirty-six patients with sepsis were randomized for treatment with placebo (n=11) or AP (n=25) and analyzed for serum creatinine levels, need for renal replacement therapy and mortality, Furthermore a subgroup (placebo n=5; AP n=11) that presented with renal failure at baseline was analyzed for these outcomes.

Serum Creatinine

At baseline and 12 h, 24 h and 48 h after intervention, serum creatinine levels were measured. FIG. 8 shows that the group of sepsis patients have increased serum creatinine levels at baseline, demonstrative for reduced renal function. FIG. 8 also shows that AP, but not placebo treatment, is able to reduce serum creatinine levels within 48 hours after initiation of treatment. This effect becomes more pronounced (FIG. 9), if only patients are included that present with renal failure (defined as serum creatinine>150 μmol/L, or already on Renal Replacement Therapy at baseline) are analyzed. It is therefore concluded that in this example, AP is able to improve renal function in sepsis patients and that the effect is more pronounced in sepsis patients that present with renal failure.

Renal Replacement Therapy

Table II shows that of all patients included in the study, 36% required renal replacement therapy (dialysis) while on placebo treatment whereas 24% of the AP treated patients needed such treatment. Of the patients already presenting with renal failure at baseline, these percentages were 80 and 27%, respectively. Therefore, the data presented in this example show that AP treatment is able to reduce the need for dialysis in sepsis patients that present with renal failure.

Mortality

During the 90 days observation period, all cause mortality in the studied population was 28% (Table II). There was a slight advantage (24% mortality) in the AP treated vs placebo treated (36%) mortality. In sepsis, however, kidney failure is the most common end-organ failure, represented in this study by the higher mortality in the subgroup that presented with renal failure (36% in the renal failure group vs 28% in all patients). Interestingly, the effect of AP in mortality reduction in the renal failure group (60% in the placebo group vs 27% in the AP treated group) was much more profound.

In this example it is shown that AP treatment (200 U/kg/24 h) improves renal function in sepsis patients presenting with reduced renal function, thereby reducing mortality and need for renal replacement therapy.

TABLE 1

Kidney function

| Kidney function parameter | Time | AP (n = 10) | Placebo (n = 5) |
|---|---|---|---|
| Total urine volume (ml) | 0-24 h | 1876 (940-2227) | 1470 (1115-2775) |
| Protein excretion (mg/day) | 0-24 h | 454 (323-533) | 447 (414-769) |
| Creatinine clearance (ml/min) | Baseline | 54 (24-84) | 80 (77-91) |
|  | 24 h | 76 (25-101) * | 59 (45-59) |
| Serum creatinine (µmol/l) | Baseline | 91 (73-138) | 99 (86-114) |
|  | 1 day | 83 (58-135) ## | 125 (71-129) |
|  | 7 days | 70 (60-90) ## | 106 (73-141) |

Data are expressed as median (25-75% range). Significantly different compared to the placebo group,
* $P < 0.05$, or compared to the baseline,
$P < 0.01$).

TABLE II

Mortality and Renal Replacement Therapy

|  | Placebo n (%) | Active n (%) | All n (%) |
|---|---|---|---|
| All patients | 11 (31) | 25 (69) | 36 (100) |
| Mortality | 4 (36) | 6 (24) | 10 (28) |
| Required RRT | 4 (36) | 6 (24) | 10 (28) |
| Sepsis with Renal Failure* | 5 (45) | 11 (44) | 16 (44) |
| Mortality | 3 (60) | 3 (27) | 6 (38) |
| Required RRT | 4 (80) | 3 (27) | 7 (44) |

RRT: renal replacement therapy
*Serum creatinine ≥150 µmol/L at baseline OR already on RRT at baseline

DESCRIPTION OF FIGURES

FIG. 10 Sequences of the four human alkaline phosphatase iso-enzymes. Note: these are the sequences of the mature proteins (i.e. without signal sequence) but before addition of the GPI-anchor and concomitant processing of the C-terminal amino acids with exception of the chimeric AP's

REFERENCES

Figure 1A:
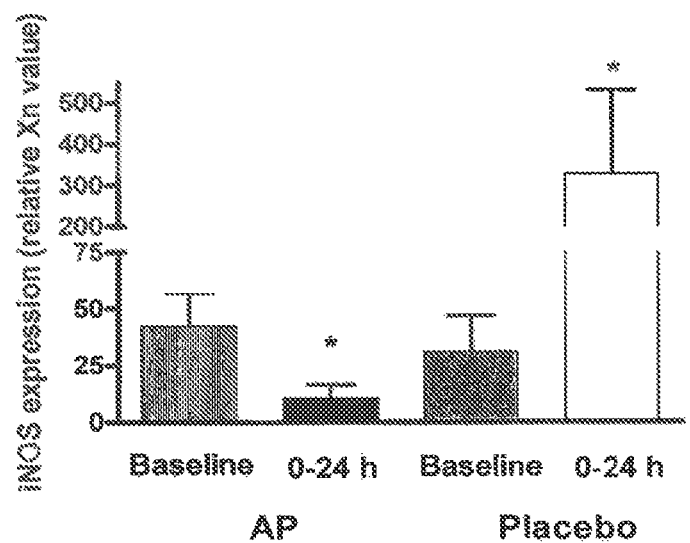
FIG. 1. Renal iNOS expression and urinary excretion of NO and GST. (A) iNOS mRNA expression is given for placebo treated (open bars, n=4) and AP treated (closed bars, n=8) patients. The relative expression of iNOS mRNA in control healthy volunteers (data not shown) was normalized for the average cycle threshold ($C_T$) value of the housekeeping gene, GAPDH ($C_T$=23.6±0.3, delta $C_T$=12.1±0.1), and set to 1. (B) NO metabolites, (C) GSTA1-1 and (D) GSTP1-1 levels in urine were measured at various times after the intervention in placebo (Δ, n=5) and AP treated patients (■, n=10). The urinary excretion of NO metabolites and GST were corrected for creatinine excretion and analyzed by ANOVA with repeated measures over the complete curve. (A) Data are expressed as mean±SE and (B+C+D) as median with 25% range for placebo and 75% range for AP. (*; significantly different compared to the placebo group, P<0.05).
Figure 1B:
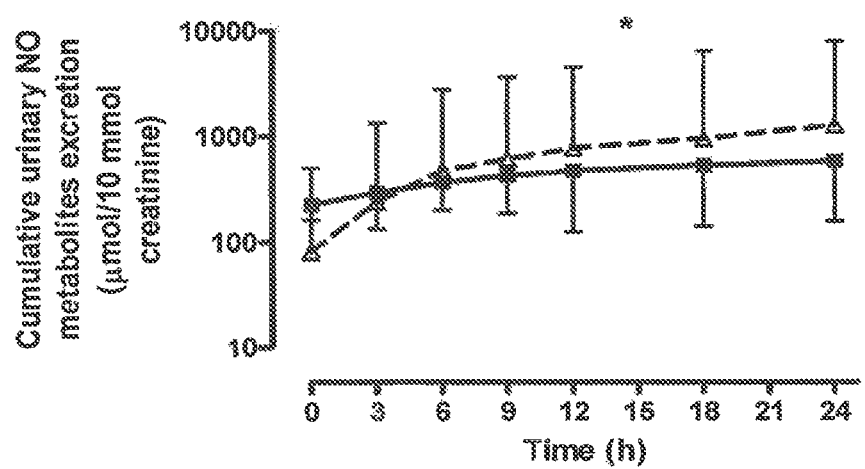
Figure 1C:
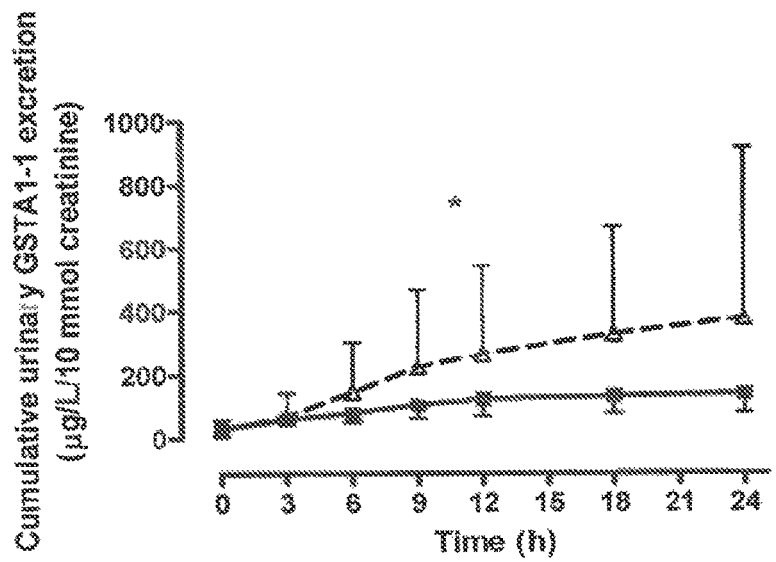
Figure 1D:
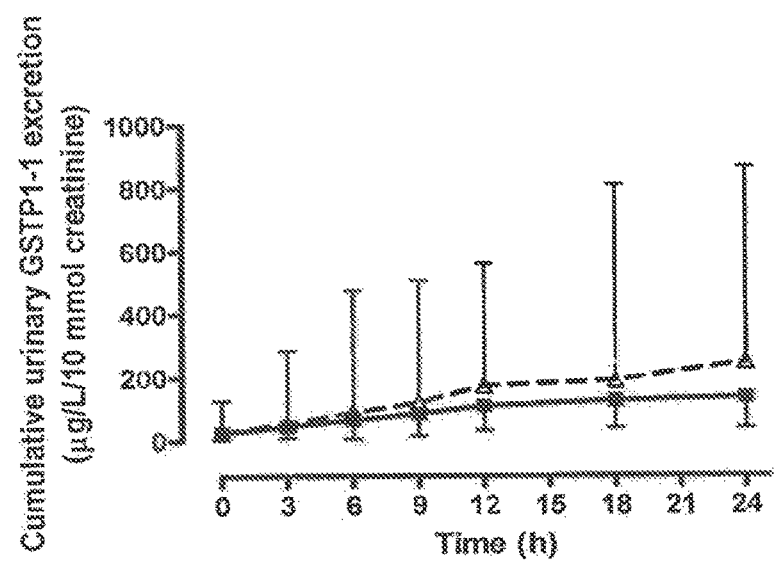
Figure 2:
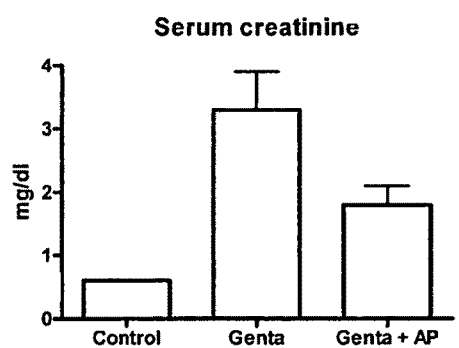
FIG. 2. Serum creatinine levels in control rats, gentamicin nephrotoxic rats and gentamicin nephrotoxic rats treated with alkaline phosphatase FIG. 3. Serum blood urea nitrogen (BUN) levels in control rats, gentamicin nephrotoxic rats and gentamicin nephrotoxic rats treated with alkaline phosphatase FIG. 4. Urine creatinine levels in control rats, gentamicin nephrotoxic rats and gentamicin nephrotoxic rats treated with alkaline phosphatase FIG. 5. Creatinine clearance in control rats, gentamicin nephrotoxic rats and gentamicin nephrotoxic rats treated with alkaline phosphatase FIG. 6. AP significantly decreases urinary protein secretion after Cisplatin nephrotoxicity. Sham: no cisplatin treatment; control treatment: Cisplatin+vehicle; AP: Cisplatin+alkaline phosphatase FIG. 7. AP decreases urinary protein secretion after Cisplatin nephrotoxicity. Sham: no cisplatin treatment; control treatment: Cisplatin+vehicle; AP: Cisplatin+alkaline phosphatase FIG. 8. AP decreases serum creatinine in sepsis patients with reduced renal function FIG. 9. AP decreases serum creatinine in sepsis patients with renal failure (defined as serum creatinine>150 µmol/L, or already on Renal Replacement Therapy at baseline)
Figure 3:
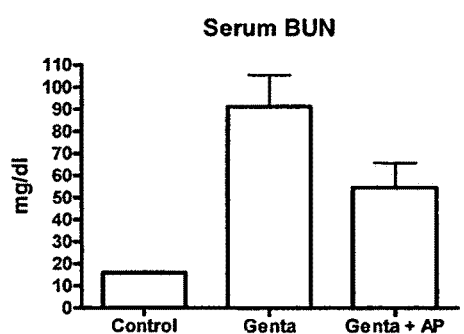
Figure 4:
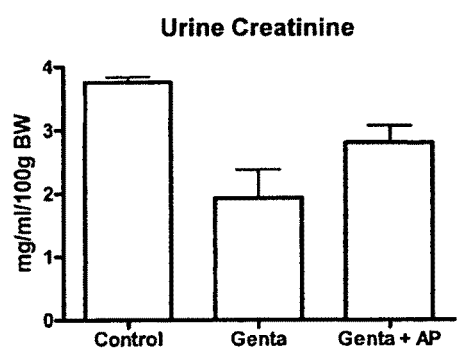
Figure 5:
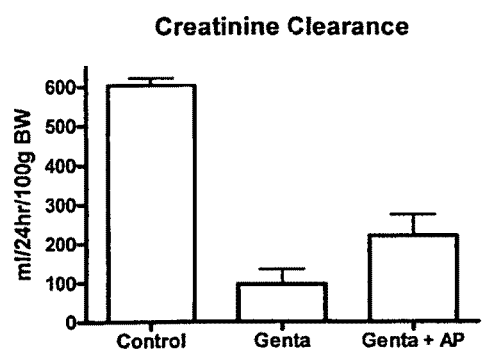
Figure 6:
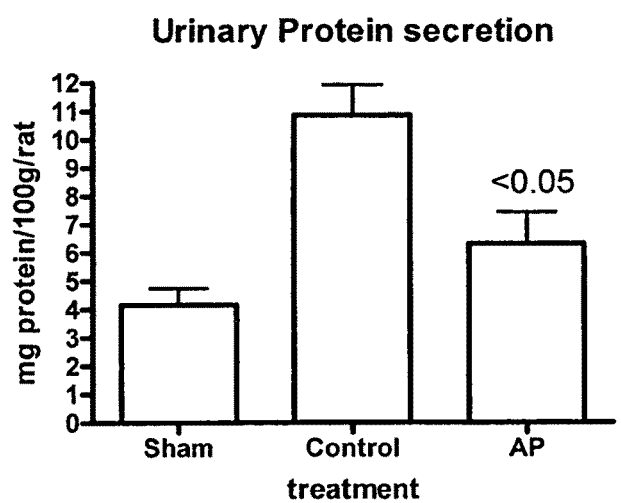
Figure 7:
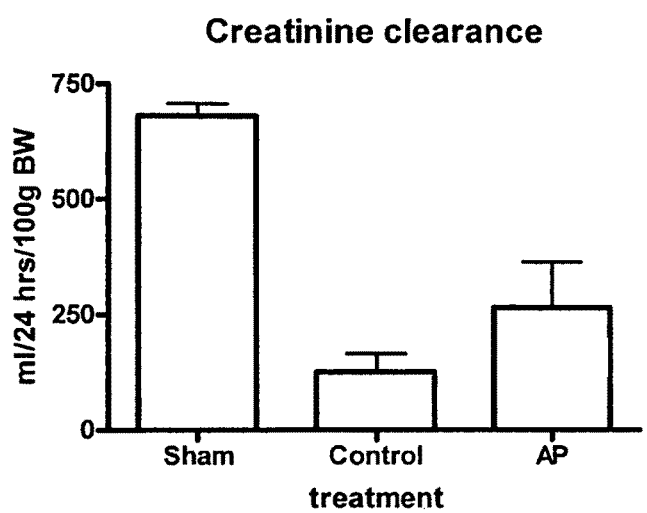
Figure 8:
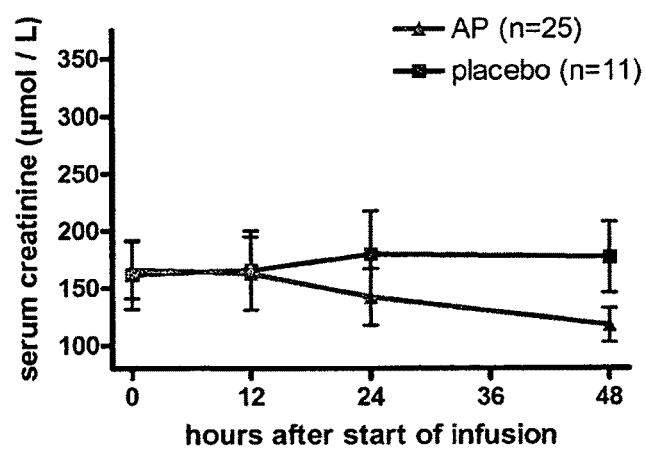
Figure 9:
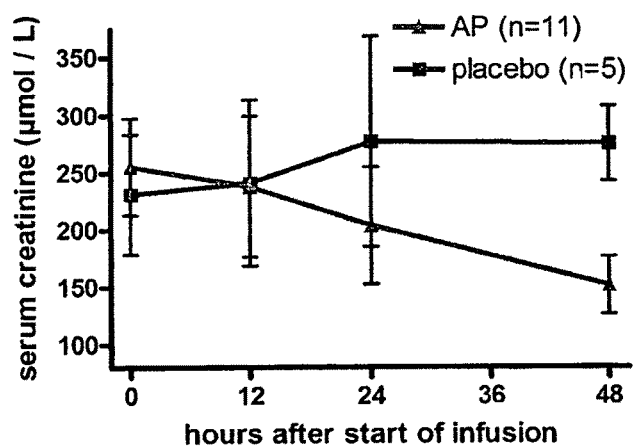

1. Hendrix P G, Hoylaerts M F, Nouwen E J and De Broe M E. Enzyme immunoassay of human placental and germ-cell alkaline phosphatase in serum. Clin Chem 1990; 36(10):1793-1799.

2. Le Du M-H, Millán J L. Structural evidence of functional divergence in human alkaline phosphatases. J Biol Chem 2002; 51:49808-49814.

6. Heemskerk S, Pickkers P, Bouw M P, Draisma A, van der Hoeven J G, Peters W H et al. Up-regulation of renal inducible nitric oxide synthase during human endotoxemia and sepsis is associated with proximal tubule injury. Clin J Am Soc Nephrol 2006; 1:853-62.

18. Moshage H, Kok B, Huizenga J R, Jansen P L. Nitrite and nitrate determinations in plasma: a critical evaluation. Clin. Chem. 1995; 41 (6 Pt 1):892-6.

19. Mulder T P, Peters W H, Court D A, Jansen J B. Sandwich ELISA for glutathione S-transferase Alpha 1-1: plasma concentrations in controls and in patients with gastrointestinal disorders. Clin. Chem. 1996; 42(3):416-9.

20. Mulder T P, Peters W H, Wobbes T, Witteman B J, Jansen J B. Measurement of glutathione S-transferase P1-1 in plasma: pitfalls and significance of screening and follow-up of patients with gastrointestinal carcinoma. Cancer 1997; 80(5):873-80.

The invention claimed is:

1. A method for treating a subject with reduced renal function due to renal failure, the method comprising: administering intravenously an effective amount of mammalian alkaline phosphatase ("AP") to a subject with reduced renal function due to renal failure.

2. The method according to claim 1, wherein the reduced renal function is induced or sustained or exacerbated due to acute renal failure.

3. The method according to claim 1, wherein the reduced renal function is induced or sustained or exacerbated by intrinsic acute renal failure.

4. The method according to claim 3, wherein the intrinsic acute renal failure is acute tubular cellular damage.

5. The method according to claim 3, wherein the intrinsic acute renal failure is glomerulonephritis.

6. The method according to claim 1, wherein the AP is human AP.

7. The method according to claim 1, wherein the AP is placental AP, placental-like AP, intestinal AP, or liver/bone/kidney AP.

8. The method according to claim 1, wherein the AP is recombinant.

9. The method according to claim 1, wherein the renal failure is chronic renal failure.

10. The method according to claim 1, wherein the renal failure is acute renal failure.

11. The method according to claim 1, wherein prior to said administration the subject has a baseline serum creatinine level of greater than 150 μmol/L or is already on renal replacement therapy.

* * * * *

SEQUENCE LISTING

<160> NUMBER OF SEQ ID NOS: 6

<210> SEQ ID NO 1
<211> LENGTH: 513
<212> TYPE: PRT
<213> ORGANISM: Homo sapiens - ALPP (placental)

<400> SEQUENCE: 1

```
Ile Ile Pro Val Glu Glu Asn Pro Asp Phe Trp Asn Arg Glu Ala
1               5                   10                  15

Ala Glu Ala Leu Gly Ala Ala Lys Lys Leu Gln Pro Ala Gln Thr Ala
                20                  25                  30

Ala Lys Asn Leu Ile Ile Phe Leu Gly Asp Gly Met Gly Val Ser Thr
                35                  40                  45

Val Thr Ala Ala Arg Ile Leu Lys Gly Gln Lys Lys Asp Lys Leu Gly
        50                  55                  60

Pro Glu Ile Pro Leu Ala Met Asp Arg Phe Pro Tyr Val Ala Leu Ser
65                  70                  75                  80

Lys Thr Tyr Asn Val Asp Lys His Val Pro Asp Ser Gly Ala Thr Ala
                85                  90                  95

Thr Ala Tyr Leu Cys Gly Val Lys Gly Asn Phe Gln Thr Ile Gly Leu
                100                 105                 110

Ser Ala Ala Ala Arg Phe Asn Gln Cys Asn Thr Thr Arg Gly Asn Glu
            115                 120                 125

Val Ile Ser Val Met Asn Arg Ala Lys Lys Ala Gly Lys Ser Val Gly
    130                 135                 140

Val Val Thr Thr Thr Arg Val Gln His Ala Ser Pro Ala Gly Thr Tyr
145                 150                 155                 160

Ala His Thr Val Asn Arg Asn Trp Tyr Ser Asp Ala Asp Val Pro Ala
                165                 170                 175

Ser Ala Arg Gln Glu Gly Cys Gln Asp Ile Ala Thr Gln Leu Ile Ser
            180                 185                 190

Asn Met Asp Ile Asp Val Ile Leu Gly Gly Gly Arg Lys Tyr Met Phe
        195                 200                 205

Arg Met Gly Thr Pro Asp Pro Glu Tyr Pro Asp Asp Tyr Ser Gln Gly
    210                 215                 220

Gly Thr Arg Leu Asp Gly Lys Asn Leu Val Gln Glu Trp Leu Ala Lys
225                 230                 235                 240

Arg Gln Gly Ala Arg Tyr Val Trp Asn Arg Thr Glu Leu Met Gln Ala
                245                 250                 255

Ser Leu Asp Pro Ser Val Thr His Leu Met Gly Leu Phe Glu Pro Gly
            260                 265                 270

Asp Met Lys Tyr Glu Ile His Arg Asp Ser Thr Leu Asp Pro Ser Leu
        275                 280                 285

Met Glu Met Thr Glu Ala Ala Leu Arg Leu Leu Ser Arg Asn Pro Arg
    290                 295                 300

Gly Phe Phe Leu Phe Val Glu Gly Gly Arg Ile Asp His Gly His His
305                 310                 315                 320

Glu Ser Arg Ala Tyr Arg Ala Leu Thr Glu Thr Ile Met Phe Asp Asp
                325                 330                 335

Ala Ile Glu Arg Ala Gly Gln Leu Thr Ser Glu Glu Asp Thr Leu Ser
            340                 345                 350

Leu Val Thr Ala Asp His Ser His Val Phe Ser Phe Gly Gly Tyr Pro
        355                 360                 365
```

```
Leu Arg Gly Ser Ser Ile Phe Gly Leu Ala Pro Gly Lys Ala Arg Asp
    370                 375                 380

Arg Lys Ala Tyr Thr Val Leu Leu Tyr Gly Asn Gly Pro Gly Tyr Val
385                 390                 395                 400

Leu Lys Asp Gly Ala Arg Pro Asp Val Thr Glu Ser Glu Ser Gly Ser
                405                 410                 415

Pro Glu Tyr Arg Gln Gln Ser Ala Val Pro Leu Asp Glu Thr His
            420                 425                 430

Ala Gly Glu Asp Val Ala Val Phe Ala Arg Gly Pro Gln Ala His Leu
            435                 440                 445

Val His Gly Val Gln Glu Gln Thr Phe Ile Ala His Val Met Ala Phe
    450                 455                 460

Ala Ala Cys Leu Glu Pro Tyr Thr Ala Cys Asp Leu Ala Pro Pro Ala
465                 470                 475                 480

Gly Thr Thr Asp Ala Ala His Pro Gly Arg Ser Val Val Pro Ala Leu
                485                 490                 495

Leu Pro Leu Leu Ala Gly Thr Leu Leu Leu Glu Thr Ala Thr Ala
                500                 505                 510

Pro

<210> SEQ ID NO 2
<211> LENGTH: 509
<212> TYPE: PRT
<213> ORGANISM: Homo sapiens - ALPI (intestinal)

<400> SEQUENCE: 2

Val Ile Pro Ala Glu Glu Asn Pro Ala Phe Trp Asn Arg Gln Ala
1               5                   10                  15

Ala Glu Ala Leu Asp Ala Ala Lys Lys Leu Gln Pro Ile Gln Lys Val
                20                  25                  30

Ala Lys Asn Leu Ile Leu Phe Leu Gly Asp Gly Leu Gly Val Pro Thr
            35                  40                  45

Val Thr Ala Thr Arg Ile Leu Lys Gly Gln Lys Asn Gly Lys Leu Gly
50                  55                  60

Pro Glu Thr Pro Leu Ala Met Asp Arg Phe Pro Tyr Leu Ala Leu Ser
65                  70                  75                  80

Lys Thr Tyr Asn Val Asp Arg Gln Val Pro Asp Ser Ala Ala Thr Ala
                85                  90                  95

Thr Ala Tyr Leu Cys Gly Val Lys Ala Asn Phe Gln Thr Ile Gly Leu
            100                 105                 110

Ser Ala Ala Ala Arg Phe Asn Gln Cys Asn Thr Thr Arg Gly Asn Glu
        115                 120                 125

Val Ile Ser Val Met Asn Arg Ala Lys Gln Ala Gly Lys Ser Val Gly
130                 135                 140

Val Val Thr Thr Thr Arg Val Gln His Ala Ser Pro Ala Gly Thr Tyr
145                 150                 155                 160

Ala His Thr Val Asn Arg Asn Trp Tyr Ser Asp Ala Asp Met Pro Ala
                165                 170                 175

Ser Ala Arg Gln Glu Gly Cys Gln Asp Ile Ala Thr Gln Leu Ile Ser
            180                 185                 190

Asn Met Asp Ile Asp Val Ile Leu Gly Gly Gly Arg Lys Tyr Met Phe
        195                 200                 205

Pro Met Gly Thr Pro Asp Pro Glu Tyr Pro Ala Asp Ala Ser Gln Asn
210                 215                 220
```

```
Gly Ile Arg Leu Asp Gly Lys Asn Leu Val Gln Glu Trp Leu Ala Lys
225                 230                 235                 240

His Gln Gly Ala Trp Tyr Val Trp Asn Arg Thr Glu Leu Met Gln Ala
                245                 250                 255

Ser Leu Asp Gln Ser Val Thr His Leu Met Gly Leu Phe Glu Pro Gly
            260                 265                 270

Asp Thr Lys Tyr Glu Ile His Arg Asp Pro Thr Leu Asp Pro Ser Leu
        275                 280                 285

Met Glu Met Thr Glu Ala Ala Leu Arg Leu Leu Ser Arg Asn Pro Arg
    290                 295                 300

Gly Phe Tyr Leu Phe Val Glu Gly Gly Arg Ile Asp His Gly His His
305                 310                 315                 320

Glu Gly Val Ala Tyr Gln Ala Leu Thr Glu Ala Val Met Phe Asp Asp
                325                 330                 335

Ala Ile Glu Arg Ala Gly Gln Leu Thr Ser Glu Glu Asp Thr Leu Thr
            340                 345                 350

Leu Val Thr Ala Asp His Ser His Val Phe Ser Phe Gly Gly Tyr Thr
        355                 360                 365

Leu Arg Gly Ser Ser Ile Phe Gly Leu Ala Pro Ser Lys Ala Gln Asp
    370                 375                 380

Ser Lys Ala Tyr Thr Ser Ile Leu Tyr Gly Asn Gly Pro Gly Tyr Val
385                 390                 395                 400

Phe Asn Ser Gly Val Arg Pro Asp Val Asn Glu Ser Glu Ser Gly Ser
                405                 410                 415

Pro Asp Tyr Gln Gln Gln Ala Ala Val Pro Leu Ser Ser Glu Thr His
            420                 425                 430

Gly Gly Glu Asp Val Ala Val Phe Ala Arg Gly Pro Gln Ala His Leu
        435                 440                 445

Val His Gly Val Gln Glu Gln Ser Phe Val Ala His Val Met Ala Phe
    450                 455                 460

Ala Ala Cys Leu Glu Pro Tyr Thr Ala Cys Asp Leu Ala Pro Pro Ala
465                 470                 475                 480

Cys Thr Thr Asp Ala Ala His Pro Val Ala Ala Ser Leu Pro Leu Leu
                485                 490                 495

Ala Gly Thr Leu Leu Leu Leu Gly Ala Ser Ala Ala Pro
            500                 505

<210> SEQ ID NO 3
<211> LENGTH: 513
<212> TYPE: PRT
<213> ORGANISM: Homo sapiens - GCAP (germ-cell or placental-like)

<400> SEQUENCE: 3

Ile Ile Pro Val Glu Glu Glu Asn Pro Asp Phe Trp Asn Arg Gln Ala
1               5                   10                  15

Ala Glu Ala Leu Gly Ala Ala Lys Lys Leu Gln Pro Ala Gln Thr Ala
                20                  25                  30

Ala Lys Asn Leu Ile Ile Phe Leu Gly Asp Gly Met Gly Val Ser Thr
            35                  40                  45

Val Thr Ala Ala Arg Ile Leu Lys Gly Gln Lys Lys Asp Lys Leu Gly
        50                  55                  60

Pro Glu Thr Phe Leu Ala Met Asp Arg Phe Pro Tyr Val Ala Leu Ser
65                  70                  75                  80

Lys Thr Tyr Ser Val Asp Lys His Val Pro Asp Ser Gly Ala Thr Ala
                85                  90                  95
```

```
Thr Ala Tyr Leu Cys Gly Val Lys Gly Asn Phe Gln Thr Ile Gly Leu
            100                 105                 110

Ser Ala Ala Ala Arg Phe Asn Gln Cys Asn Thr Thr Arg Gly Asn Glu
            115                 120                 125

Val Ile Ser Val Met Asn Arg Ala Lys Lys Ala Gly Lys Ser Val Gly
130                 135                 140

Val Val Thr Thr Thr Arg Val Gln His Ala Ser Pro Ala Gly Ala Tyr
145                 150                 155                 160

Ala His Thr Val Asn Arg Asn Trp Tyr Ser Asp Ala Asp Val Pro Ala
                165                 170                 175

Ser Ala Arg Gln Glu Gly Cys Gln Asp Ile Ala Thr Gln Leu Ile Ser
            180                 185                 190

Asn Met Asp Ile Asp Val Ile Leu Gly Gly Gly Arg Lys Tyr Met Phe
            195                 200                 205

Pro Met Gly Thr Pro Asp Pro Glu Tyr Pro Asp Tyr Ser Gln Gly
            210                 215                 220

Gly Thr Arg Leu Asp Gly Lys Asn Leu Val Gln Glu Trp Leu Ala Lys
225                 230                 235                 240

His Gln Gly Ala Arg Tyr Val Trp Asn Arg Thr Glu Leu Leu Gln Ala
                245                 250                 255

Ser Leu Asp Pro Ser Val Thr His Leu Met Gly Leu Phe Glu Pro Gly
            260                 265                 270

Asp Met Lys Tyr Glu Ile His Arg Asp Ser Thr Leu Asp Pro Ser Leu
            275                 280                 285

Met Glu Met Thr Glu Ala Ala Leu Leu Leu Leu Ser Arg Asn Pro Arg
290                 295                 300

Gly Phe Phe Leu Phe Val Glu Gly Gly Arg Ile Asp His Gly His His
305                 310                 315                 320

Glu Ser Arg Ala Tyr Arg Ala Leu Thr Glu Thr Ile Met Phe Asp Asp
                325                 330                 335

Ala Ile Glu Arg Ala Gly Gln Leu Thr Ser Glu Glu Asp Thr Leu Ser
            340                 345                 350

Leu Val Thr Ala Asp His Ser His Val Phe Ser Phe Gly Gly Tyr Pro
            355                 360                 365

Leu Arg Gly Ser Ser Ile Phe Gly Leu Ala Pro Gly Lys Ala Arg Asp
            370                 375                 380

Arg Lys Ala Tyr Thr Val Leu Leu Tyr Gly Asn Gly Pro Gly Tyr Val
385                 390                 395                 400

Leu Lys Asp Gly Ala Arg Pro Asp Val Thr Glu Ser Glu Ser Gly Ser
            405                 410                 415

Pro Glu Tyr Arg Gln Gln Ser Ala Val Pro Leu Asp Gly Glu Thr His
            420                 425                 430

Ala Gly Glu Asp Val Ala Val Phe Ala Arg Gly Pro Gln Ala His Leu
            435                 440                 445

Val His Gly Val Gln Glu Gln Thr Phe Ile Ala His Val Met Ala Phe
            450                 455                 460

Ala Ala Cys Leu Glu Pro Tyr Thr Ala Cys Asp Leu Ala Pro Arg Ala
465                 470                 475                 480

Gly Thr Thr Asp Ala Ala His Pro Gly Pro Ser Val Val Pro Ala Leu
            485                 490                 495

Leu Pro Leu Leu Ala Gly Thr Leu Leu Leu Leu Gly Thr Ala Thr Ala
            500                 505                 510

Pro
```

```
<210> SEQ ID NO 4
<211> LENGTH: 507
<212> TYPE: PRT
<213> ORGANISM: Homo sapiens - (tissue non specific)

<400> SEQUENCE: 4

Leu Val Pro Glu Lys Glu Lys Asp Pro Lys Tyr Trp Arg Asp Gln Ala
 1               5                  10                  15

Gln Glu Thr Leu Lys Tyr Ala Leu Glu Leu Gln Lys Leu Asn Thr Asn
             20                  25                  30

Val Ala Lys Asn Val Ile Met Phe Leu Gly Asp Gly Met Gly Val Ser
         35                  40                  45

Thr Val Thr Ala Ala Arg Ile Leu Lys Gly Gln Leu His His Asn Pro
     50                  55                  60

Gly Glu Glu Thr Arg Leu Glu Met Asp Lys Phe Pro Phe Val Ala Leu
 65                  70                  75                  80

Ser Lys Thr Tyr Asn Thr Asn Ala Gln Val Pro Asp Ser Ala Gly Thr
                 85                  90                  95

Ala Thr Ala Tyr Leu Cys Gly Val Lys Ala Asn Glu Gly Thr Val Gly
            100                 105                 110

Val Ser Ala Ala Thr Glu Arg Ser Arg Cys Asn Thr Thr Gln Gly Asn
        115                 120                 125

Glu Val Thr Ser Ile Leu Arg Trp Ala Lys Asp Ala Gly Lys Ser Val
    130                 135                 140

Gly Ile Val Thr Thr Thr Arg Val Asn His Ala Thr Pro Ser Ala Ala
145                 150                 155                 160

Tyr Ala His Ser Ala Asp Arg Asp Trp Tyr Ser Asp Asn Glu Met Pro
                165                 170                 175

Pro Glu Ala Leu Ser Gln Gly Cys Lys Asp Ile Ala Tyr Gln Leu Met
            180                 185                 190

His Asn Ile Arg Asp Ile Asp Val Ile Met Gly Gly Gly Arg Lys Tyr
        195                 200                 205

Met Tyr Pro Lys Asn Lys Thr Asp Val Glu Tyr Glu Ser Asp Glu Lys
    210                 215                 220

Ala Arg Gly Thr Arg Leu Asp Gly Leu Asp Leu Val Asp Thr Trp Lys
225                 230                 235                 240

Ser Phe Lys Pro Arg His Lys His Ser His Phe Ile Trp Asn Arg Thr
                245                 250                 255

Glu Leu Leu Thr Leu Asp Pro His Asn Val Asp Tyr Leu Leu Gly Leu
            260                 265                 270

Phe Glu Pro Gly Asp Met Gln Tyr Glu Leu Asn Arg Asn Asn Val Thr
        275                 280                 285

Asp Pro Ser Leu Ser Glu Met Val Val Ala Ile Gln Ile Leu Arg
    290                 295                 300

Lys Asn Pro Lys Gly Phe Phe Leu Leu Val Glu Gly Gly Arg Ile Asp
305                 310                 315                 320

His Gly His His Glu Gly Lys Ala Lys Gln Ala Leu His Glu Ala Val
                325                 330                 335

Glu Met Asp Arg Ala Ile Gly Gln Ala Gly Ser Leu Thr Ser Ser Glu
            340                 345                 350

Asp Thr Leu Thr Val Val Thr Ala Asp His Ser His Val Phe Thr Phe
        355                 360                 365

Gly Gly Tyr Thr Pro Arg Gly Asn Ser Ile Phe Gly Leu Ala Pro Met
    370                 375                 380
```

-continued

```
Leu Ser Asp Thr Asp Lys Lys Pro Phe Thr Ala Ile Leu Tyr Gly Asn
385                 390                 395                 400

Gly Pro Gly Tyr Lys Val Val Gly Gly Glu Arg Glu Asn Val Ser Met
                405                 410                 415

Val Asp Tyr Ala His Asn Asn Tyr Gln Ala Gln Ser Ala Val Pro Leu
            420                 425                 430

Arg His Glu Thr His Gly Gly Glu Asp Val Ala Val Phe Ser Lys Gly
        435                 440                 445

Pro Met Ala His Leu Leu His Gly Val His Glu Gln Asn Tyr Val Pro
    450                 455                 460

His Val Met Ala Tyr Ala Ala Cys Ile Gly Ala Asn Leu Gly His Cys
465                 470                 475                 480

Ala Pro Ala Ser Ser Ala Gly Ser Leu Ala Ala Gly Pro Leu Leu Leu
                485                 490                 495

Ala Leu Ala Leu Tyr Pro Leu Ser Val Leu Phe
                500                 505

<210> SEQ ID NO 5
<211> LENGTH: 484
<212> TYPE: PRT
<213> ORGANISM: Homo sapiens - ALPI/PLAP (chimera)

<400> SEQUENCE: 5

Val Ile Pro Ala Glu Glu Glu Asn Pro Ala Phe Trp Asn Arg Gln Ala
1               5                   10                  15

Ala Glu Ala Leu Asp Ala Ala Lys Lys Leu Gln Pro Ile Gln Lys Val
                20                  25                  30

Ala Lys Asn Leu Ile Leu Phe Leu Gly Asp Gly Leu Gly Val Pro Thr
                35                  40                  45

Val Thr Ala Thr Arg Ile Leu Lys Gly Gln Lys Asn Gly Lys Leu Gly
        50                  55                  60

Pro Glu Thr Pro Leu Ala Met Asp Arg Phe Pro Tyr Leu Ala Leu Ser
65                  70                  75                  80

Lys Thr Tyr Asn Val Asp Arg Gln Val Pro Asp Ser Ala Ala Thr Ala
                85                  90                  95

Thr Ala Tyr Leu Cys Gly Val Lys Ala Asn Phe Gln Thr Ile Gly Leu
                100                 105                 110

Ser Ala Ala Ala Arg Phe Asn Gln Cys Asn Thr Thr Arg Gly Asn Glu
            115                 120                 125

Val Ile Ser Val Met Asn Arg Ala Lys Gln Ala Gly Lys Ser Val Gly
    130                 135                 140

Val Val Thr Thr Thr Arg Val Gln His Ala Ser Pro Ala Gly Thr Tyr
145                 150                 155                 160

Ala His Thr Val Asn Arg Asn Trp Tyr Ser Asp Ala Asp Met Pro Ala
                165                 170                 175

Ser Ala Arg Gln Glu Gly Cys Gln Asp Ile Ala Thr Gln Leu Ile Ser
            180                 185                 190

Asn Met Asp Ile Asp Val Ile Leu Gly Gly Gly Arg Lys Tyr Met Phe
        195                 200                 205

Pro Met Gly Thr Pro Asp Pro Glu Tyr Pro Ala Asp Ala Ser Gln Asn
    210                 215                 220

Gly Ile Arg Leu Asp Gly Lys Asn Leu Val Gln Glu Trp Leu Ala Lys
225                 230                 235                 240

His Gln Gly Ala Trp Tyr Val Trp Asn Arg Thr Glu Leu Met Gln Ala
                245                 250                 255
```

```
Ser Leu Asp Gln Ser Val Thr His Leu Met Gly Leu Phe Glu Pro Gly
        260                 265                 270

Asp Thr Lys Tyr Glu Ile His Arg Asp Pro Thr Leu Asp Pro Ser Leu
    275                 280                 285

Met Glu Met Thr Glu Ala Ala Leu Arg Leu Ser Arg Asn Pro Arg
290                 295                 300

Gly Phe Tyr Leu Phe Val Glu Gly Gly Arg Ile Asp His Gly His His
305                 310                 315                 320

Glu Gly Val Ala Tyr Gln Ala Leu Thr Glu Ala Val Met Phe Asp Asp
                325                 330                 335

Ala Ile Glu Arg Ala Gly Gln Leu Thr Ser Glu Glu Asp Thr Leu Thr
        340                 345                 350

Leu Val Thr Ala Asp His Ser His Val Phe Ser Phe Gly Gly Tyr Pro
                355                 360                 365

Leu Arg Gly Ser Ser Ile Phe Gly Leu Ala Pro Gly Lys Ala Arg Asp
    370                 375                 380

Arg Lys Ala Tyr Thr Val Leu Leu Tyr Gly Asn Gly Pro Gly Tyr Val
385                 390                 395                 400

Leu Lys Asp Gly Ala Arg Pro Asp Val Thr Glu Ser Glu Ser Gly Ser
                405                 410                 415

Pro Glu Tyr Arg Gln Gln Ser Ala Val Pro Leu Asp Glu Glu Thr His
                420                 425                 430

Gly Gly Glu Asp Val Ala Val Phe Ala Arg Gly Pro Gln Ala His Leu
            435                 440                 445

Val His Gly Val Gln Glu Gln Ser Phe Val Ala His Val Met Ala Phe
450                 455                 460

Ala Ala Cys Leu Glu Pro Tyr Thr Ala Cys Asp Leu Ala Pro Pro Ala
465                 470                 475                 480

Cys Thr Thr Asp

<210> SEQ ID NO 6
<211> LENGTH: 484
<212> TYPE: PRT
<213> ORGANISM: Homo sapiens - ALPP/ALPI (chimera)

<400> SEQUENCE: 6

Ile Ile Pro Val Glu Glu Glu Asn Pro Asp Phe Trp Asn Arg Glu Ala
1               5                   10                  15

Ala Glu Ala Leu Gly Ala Ala Lys Lys Leu Gln Pro Ala Gln Thr Ala
                20                  25                  30

Ala Lys Asn Leu Ile Ile Phe Leu Gly Asp Gly Met Gly Val Ser Thr
            35                  40                  45

Val Thr Ala Ala Arg Ile Leu Lys Gly Gln Lys Lys Asp Lys Leu Gly
    50                  55                  60

Pro Glu Ile Pro Leu Ala Met Asp Arg Phe Pro Tyr Val Ala Leu Ser
65                  70                  75                  80

Lys Thr Tyr Asn Val Asp Lys His Val Pro Asp Ser Gly Ala Thr Ala
                85                  90                  95

Thr Ala Tyr Leu Cys Gly Val Lys Gly Asn Phe Gln Thr Ile Gly Leu
            100                 105                 110

Ser Ala Ala Ala Arg Phe Asn Gln Cys Asn Thr Thr Arg Gly Asn Glu
        115                 120                 125

Val Ile Ser Val Met Asn Arg Ala Lys Lys Ala Gly Lys Ser Val Gly
    130                 135                 140

Val Val Thr Thr Thr Arg Val Gln His Ala Ser Pro Ala Gly Thr Tyr
```

-continued

```
            145                 150                 155                 160
        Ala His Thr Val Asn Arg Asn Trp Tyr Ser Asp Ala Asp Val Pro Ala
                        165                 170                 175

Ser Ala Arg Gln Glu Gly Cys Gln Asp Ile Ala Thr Gln Leu Ile Ser
                        180                 185                 190

Asn Met Asp Ile Asp Val Ile Leu Gly Gly Gly Arg Lys Tyr Met Phe
                        195                 200                 205

Arg Met Gly Thr Pro Asp Pro Glu Tyr Pro Asp Tyr Ser Gln Gly
                        210                 215                 220

Gly Thr Arg Leu Asp Gly Lys Asn Leu Val Gln Glu Trp Leu Ala Lys
        225                 230                 235                 240

Arg Gln Gly Ala Arg Tyr Val Trp Asn Arg Thr Glu Leu Met Gln Ala
                        245                 250                 255

Ser Leu Asp Pro Ser Val Thr His Leu Met Gly Leu Phe Glu Pro Gly
                        260                 265                 270

Asp Met Lys Tyr Glu Ile His Arg Asp Ser Thr Leu Asp Pro Ser Leu
                        275                 280                 285

Met Glu Met Thr Glu Ala Ala Leu Arg Leu Leu Ser Arg Asn Pro Arg
                        290                 295                 300

Gly Phe Phe Leu Phe Val Glu Gly Gly Arg Ile Asp His Gly His His
        305                 310                 315                 320

Glu Ser Arg Ala Tyr Arg Ala Leu Thr Glu Thr Ile Met Phe Asp Asp
                        325                 330                 335

Ala Ile Glu Arg Ala Gly Gln Leu Thr Ser Glu Glu Asp Thr Leu Ser
                        340                 345                 350

Leu Val Thr Ala Asp His Ser His Val Phe Ser Phe Gly Gly Tyr Thr
                        355                 360                 365

Leu Arg Gly Ser Ser Ile Phe Gly Leu Ala Pro Ser Lys Ala Gln Asp
                        370                 375                 380

Ser Lys Ala Tyr Thr Ser Ile Leu Tyr Gly Asn Gly Pro Gly Tyr Val
        385                 390                 395                 400

Phe Asn Ser Gly Val Arg Pro Asp Val Asn Glu Ser Glu Ser Gly Ser
                        405                 410                 415

Pro Asp Tyr Gln Gln Gln Ala Ala Val Pro Leu Ser Ser Glu Thr His
                        420                 425                 430

Ala Gly Glu Asp Val Ala Val Phe Ala Arg Gly Pro Gln Ala His Leu
                        435                 440                 445

Val His Gly Val Gln Glu Gln Thr Phe Ile Ala His Val Met Ala Phe
                        450                 455                 460

Ala Ala Cys Leu Glu Pro Thr Tyr Ala Cys Asp Leu Ala Pro Pro Ala
        465                 470                 475                 480

Gly Thr Thr Asp
```